US012440365B2

(12) United States Patent
Zimmer et al.

(10) Patent No.: US 12,440,365 B2
(45) Date of Patent: *Oct. 14, 2025

(54) ORTHOPEDIC BRACE HAVING TELESCOPIC LATERAL PANELS AND AN ADJUSTABLE PULLEY SUBSYSTEM

(71) Applicant: Aspen Medical Products, LLC, Irvine, CA (US)

(72) Inventors: Erik Zimmer, Oceanside, CA (US); Jane Price, Anaheim, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 335 days.

This patent is subject to a terminal disclaimer.

(21) Appl. No.: 18/162,328

(22) Filed: Jan. 31, 2023

(65) Prior Publication Data

US 2023/0285175 A1 Sep. 14, 2023

Related U.S. Application Data

(60) Provisional application No. 63/305,671, filed on Feb. 1, 2022, provisional application No. 63/305,678, filed on Feb. 1, 2022.

(51) Int. Cl.
*A61F 5/02* (2006.01)

(52) U.S. Cl.
CPC .............. *A61F 5/022* (2013.01); *A61F 5/028* (2013.01)

(58) Field of Classification Search
CPC ........ A61F 5/022; A61F 5/028; A61F 5/0193; A61F 5/024; A61F 5/026; A61F 5/03; A61F 5/02–03; A61F 5/055; A41D 13/0506–0537; A41C 1/00; A41C 1/08; A41C 1/10; A41C 1/12; A41C 1/14
USPC ............... 602/12, 5, 19; 128/96.1, 99.1, 846
See application file for complete search history.

(56) References Cited

U.S. PATENT DOCUMENTS 2,973,030 A 2/1961 Matthewson
5,964,722 A 10/1999 Goralnik et al.
6,500,137 B1 * 12/2002 Molino .................. A61F 5/022 602/19

(Continued)

FOREIGN PATENT DOCUMENTS

FR 2992168 A1 12/2013

OTHER PUBLICATIONS

PCT/US2023/012132 filed Feb. 1, 2023 International Search Report and Written Opinion dated Apr. 14, 2023.

(Continued)

*Primary Examiner* — Rachael E Bredefeld
*Assistant Examiner* — Seth R. Brown
(74) *Attorney, Agent, or Firm* — Rutan & Tucker, LLP

(57) ABSTRACT

An orthopedic brace features a belt brace and an adjustable spinal support extension. The belt brace includes a structural member. The adjustable spinal support extension is configured for insertion into the structural member. The adjustable spinal support extension includes a sleeve, a first strut member, and a second strut member adjustably coupled to the first strut member to alter a length of the spinal support extension. The first strut member and the second strut member are partially enclosed within the sleeve and a fastener of the structural member is attachable to a fastener on the sleeve when the adjustable spinal support extension is placed within the sleeve.

25 Claims, 17 Drawing Sheets

(56) References Cited

U.S. PATENT DOCUMENTS

| | | | | |
|---|---|---|---|---|
| 6,676,620 | B2 * | 1/2004 | Schwenn | A61F 5/028 602/19 |
| 7,001,348 | B2 * | 2/2006 | Garth | A61F 5/02 602/5 |
| 7,608,052 | B1 | 10/2009 | Baker | |
| 8,172,779 | B2 | 5/2012 | Ingimundarson et al. | |
| 8,216,167 | B2 | 7/2012 | Garth et al. | |
| 8,556,840 | B2 | 10/2013 | Burke et al. | |
| 8,795,214 | B1 * | 8/2014 | Conti | A61F 5/02 602/5 |
| 9,220,625 | B2 | 12/2015 | Ingimundarson et al. | |
| 9,504,596 | B1 * | 11/2016 | Kozersky | A61F 5/028 |
| 10,070,985 | B2 | 9/2018 | Glazener et al. | |
| 10,231,862 | B2 | 3/2019 | Summit et al. | |
| 10,238,524 | B2 | 3/2019 | Burke et al. | |
| 11,273,065 | B2 * | 3/2022 | Garth | A61F 5/34 |
| 2002/0198481 | A1 | 12/2002 | Humphries | |
| 2003/0208147 | A1 * | 11/2003 | Reinecke | A61F 5/024 602/19 |
| 2004/0077981 | A1 | 4/2004 | Weaver et al. | |
| 2004/0220503 | A1 | 11/2004 | Kozersky | |
| 2010/0168630 | A1 | 7/2010 | Cropper et al. | |
| 2010/0298749 | A1 | 11/2010 | Garth et al. | |
| 2011/0077567 | A1 | 3/2011 | Bledsoe | |
| 2012/0209162 | A1 | 8/2012 | Bar-Natan et al. | |
| 2012/0253251 | A1 * | 10/2012 | Thornton | A61F 5/028 602/19 |
| 2014/0100501 | A1 | 4/2014 | Burke et al. | |
| 2014/0276311 | A1 | 9/2014 | Hollister et al. | |
| 2014/0371646 | A1 | 12/2014 | Kozersky | |
| 2015/0290019 | A1 | 10/2015 | Garth et al. | |
| 2016/0045387 | A1 | 2/2016 | Lee et al. | |
| 2016/0089554 | A1 | 3/2016 | Perner | |
| 2016/0151190 | A1 | 6/2016 | Lurssen et al. | |
| 2016/0206467 | A1 * | 7/2016 | Glace | A61F 5/02 |
| 2016/0324678 | A1 | 11/2016 | Ingimundarson et al. | |
| 2017/0348134 | A1 | 12/2017 | Joseph et al. | |
| 2018/0303699 | A1 | 10/2018 | Romo et al. | |
| 2018/0325184 | A1 | 11/2018 | Roberts | |
| 2018/0353314 | A1 * | 12/2018 | Grim | A61F 5/028 |
| 2019/0070033 | A1 | 3/2019 | Heronen et al. | |
| 2020/0179153 | A1 | 6/2020 | Wang | |
| 2022/0226139 | A1 * | 7/2022 | Poker | A61F 5/022 |

OTHER PUBLICATIONS

U.S. Appl. No. 18/162,383, filed Jan. 31, 2023, Non-Final Office Action dated Mar. 31, 2025.

U.S. Appl. No. 18/162,367, filed Jan. 31, 2023, Non-Final Office Action dated Jun. 16, 2025.

U.S. Appl. No. 18/162,345, filed Jan. 31, 2023, Non-Final Office Action dated May 20, 2025.

* cited by examiner

FIG. 2A
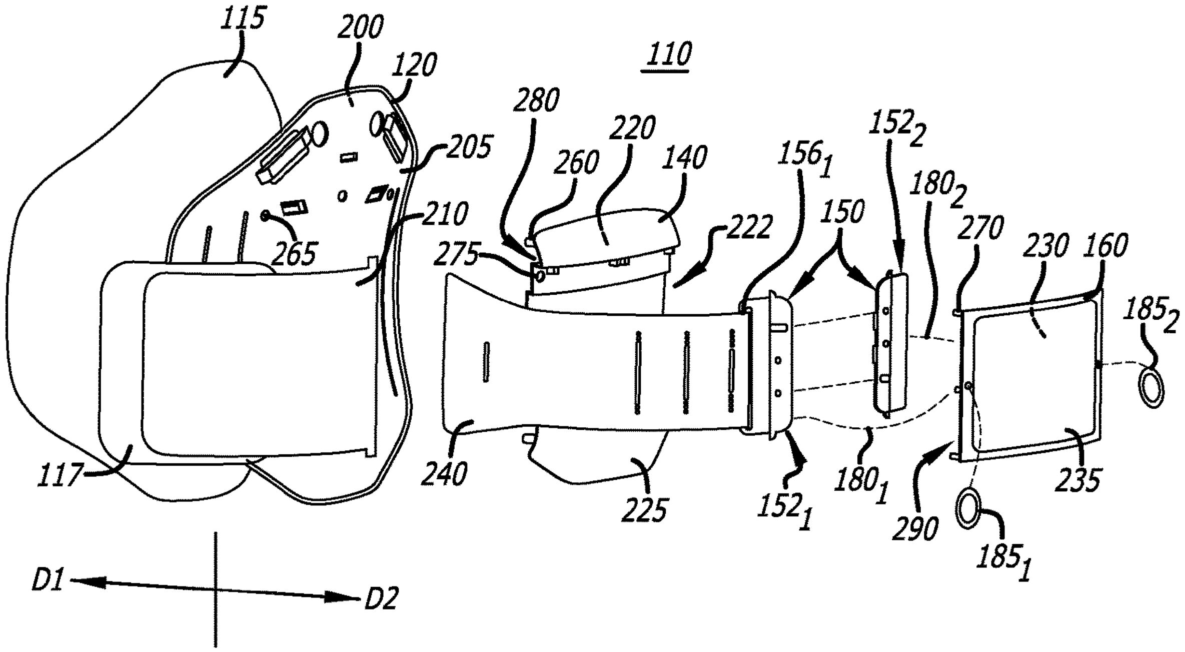
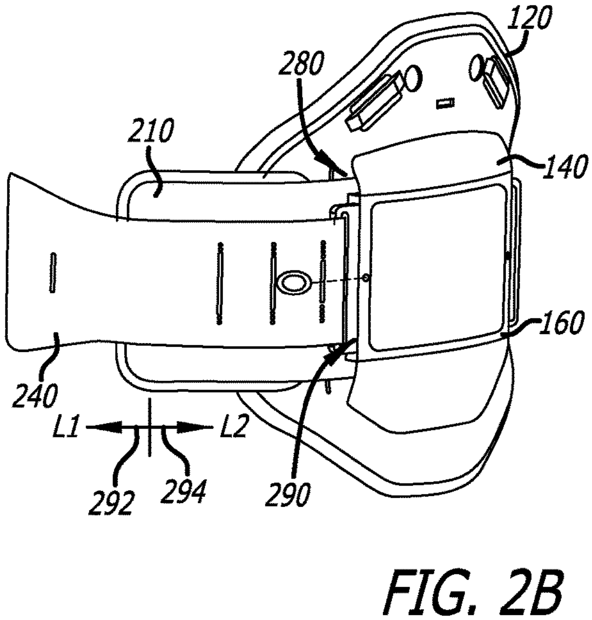
FIG. 2B

ORTHOPEDIC BRACE HAVING TELESCOPIC LATERAL PANELS AND AN ADJUSTABLE PULLEY SUBSYSTEM

CROSS-REFERENCE TO RELATED APPLICATIONS

This application claims the benefit of priority on U.S. Provisional Application No. 63/305,671 filed Feb. 1, 2022 and U.S. Provisional Application No. 63/305,678 filed Feb. 1, 2022, the entire contents of both of which are incorporated by reference herein.

FIELD

Embodiments of the disclosure relate to the field of medical devices. More specifically, one embodiment of the disclosure relates to an orthopedic brace and components thereof.

General Background

The following description includes information that may be useful in understanding the described invention. It is not an admission that any of the information provided herein is prior art or relevant to the presently claimed invention, or that any publication specifically or implicitly referenced is prior art.

Orthopedic braces (orthoses) usually need to be adjusted or customized in some manner to conform to the body part(s) being braced, and then properly positioned. A typical orthosis commonly has at least two portions, a rigid portion supporting a body part, and a flexible or semi-flexible portion securing the orthosis to the body. One type of orthopedic brace is referred to as a "thoracic-lumbar-sacral orthosis" or by the acronym "TLSO."

A TLSO is a brace that limits movement in a wearer's spine from the thoracic area (mid-back area) to the wearer's sacrum (lower-back area). At the same time, the TLSO allows a wearer's neck to move freely. This type of brace is normally used to provide support and stabilization of the spine after a back injury and/or surgery, and in some cases, may be utilized to address spinal pathologies.

One common problem associated with conventional TLSOs is the donning process is quite difficult, especially when the orthotist is trying to ensure that the TLSO properly fits to immobilize the patient as a proper fit of the orthosis normally provides the wearer with improved pain reduction and promotes healing. Conventional TLSOs rely on soft goods, namely a long belt extending from the posterior brace with a hook and loop fastener that is affixed to a complementary hook and loop fastener located on a top surface of the anterior brace, to secure the anterior brace to the posterior brace. Hence, the donning process may require the patient to be "log rolled" (moved face-down to face-up or vice versa) multiple times in order to adjust and fit the TLSO onto the patient. For example, the patient would be placed onto the posterior bracing system, then "log rolled" onto an anterior brace to allow the belt to be sized with excess belt strap being hidden. Thereafter, the patient may be "log rolled" one or more times to adjust the posterior bracing system or belt adjustment to better immobilize the patient. Avoidance of a complex (and in some cases painful) donning process would ensure more effective usage of TLSO-based orthopedic braces.

Furthermore, there are different braces for different conditions, including the usage of an orthopedic brace with a cervical collar, referred to as Cervical Thoracic Lumbar Sacral Orthosis (CTLSO). It would be advantageous to provide an orthopedic brace that features a uniform construction to enable transitioning from a TLSO to a CTLSO and vice versa.

BRIEF DESCRIPTION OF THE DRAWINGS

Embodiments of the invention are illustrated by way of example and not by way of limitation in the figures of the accompanying drawings, in which like references indicate similar elements and in which:

FIG. 2A is an exploded view of the exemplary embodiment of the posterior bracing system of FIG. 1.

FIG. 2B is an exemplary embodiment of the posterior bracing system of FIG. 1 with liner padding for donning.

DETAILED DESCRIPTION

Figure 1:
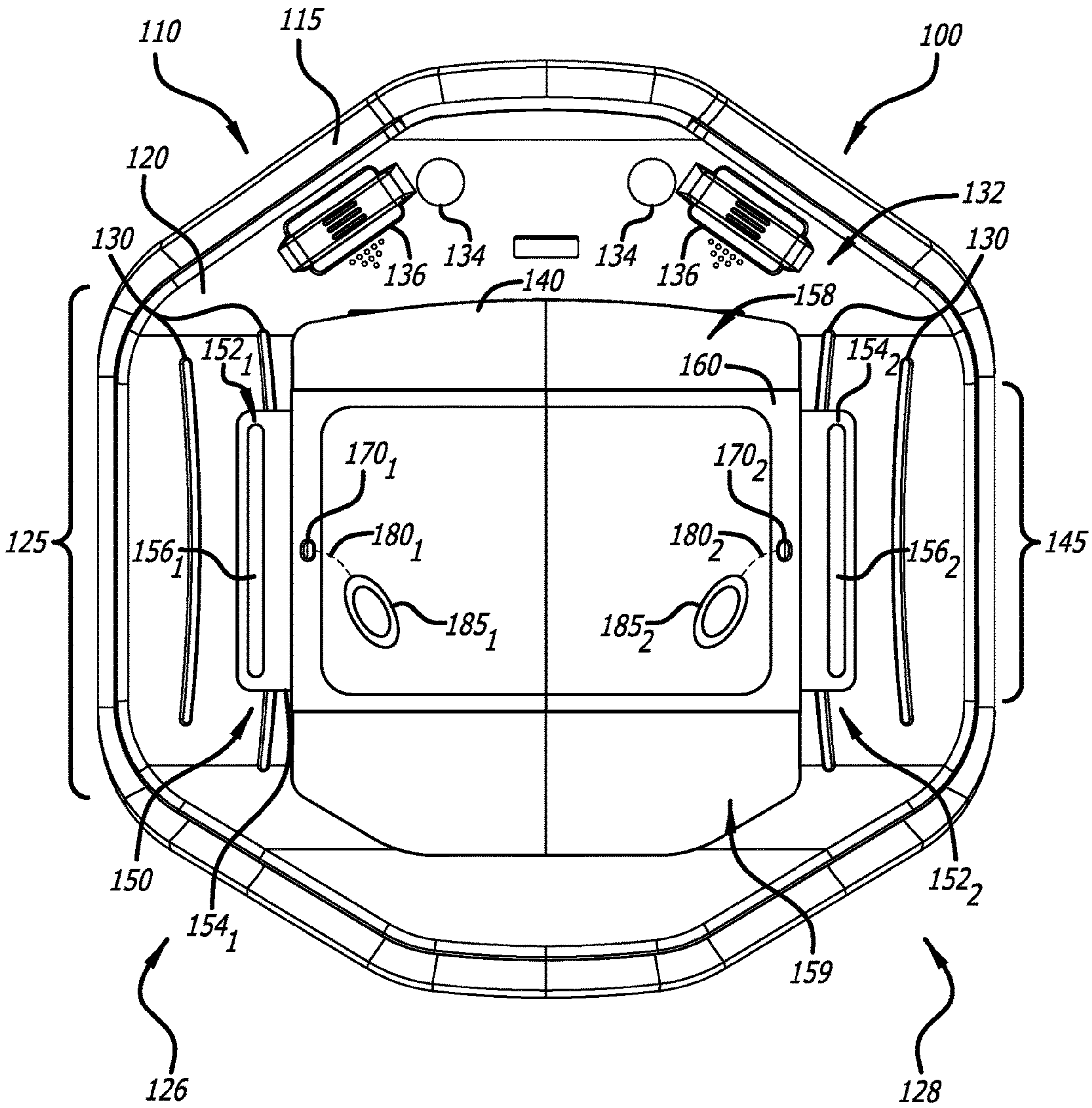
FIG. 1 is a perspective rear view of an exemplary embodiment of an orthopedic brace with a posterior bracing system.

Embodiments of the present disclosure generally relate to an orthopedic brace including a posterior bracing system. According to one embodiment of the disclosure, the posterior bracing system features an orthosis fastening subsystem, which includes telescopic lateral panels that extend from opposite sides of the posterior bracing system and operate in concert with an adjustable belt to assist in donning of the orthopedic brace onto the patient. As described herein, the orthopedic brace may constitute any type of lumbar sacral orthosis (LSO), including a standard LSO (lower back brace belt) or other orthoses configured to provide greater patient immobilization, such as a thoracic LSO (TLSO), or a cervical TLSO (CTLSO) as described below.

When deployed as a TLSO or CTLSO or LSO, the posterior bracing system for the orthopedic brace may be configured in accordance with a layered component architecture including a posterior panel, a posterior cover, and a pulley cover. Each of these components may be formed with a rigid material, such as hardened plastic for example, to provide greater stiffness for immobilization of the patient. Herein, the posterior panel is shaped and sized to rest again the mid-to-lower portions of the patient's back to partially immobilize the spine of the patient. The posterior cover is sized to overlay a midsection area of the posterior panel, while the pulley cover is sized to overlay a midsection area of the posterior cover. This layered architecture creates distinct chambers for housing different components forming the orthosis fastening subsystem. For example, the posterior panel and posterior cover create a first chamber for housing and securing end portions of lateral (side) panels that can be slidably extended in a telescopic manner from side openings in the first chamber. Similarly, the posterior cover and the pulley cover create a second chamber for housing a pulley subsystem to which adjustable belt members are attached along with the telescopic lateral panels.

According to one embodiment of the disclosure, as an illustrative example, the posterior cover is positioned to partially overlay a rear surface of the posterior panel, such as a midsection of the posterior panel. As a result, the first chamber is created between the front (anterior facing) surface of the posterior cover and the rear (posterior facing) surface of the posterior panel. Additionally, the pulley cover is positioned to partially overlay a rear surface of the posterior cover, such as covering a recessed area formed as part of the posterior cover. As a result, a second chamber is created between the front (anterior) surface of the pulley cover and the rear (posterior) surface of the posterior cover.

Herein, a back of a patient may be positioned against a liner (padding) placed on a front (anterior) surface of the posterior panel. The front surface of the posterior panel is shaped with a contour that conforms with thoracic and lumbar regions of a patient's spine. A rear (posterior) surface of the posterior panel includes a first concave region that, in combination with the front surface of the posterior cover, creates the first chamber. The posterior cover includes posts that are coupled to the posterior panel, where such coupling may be realized by insertion of the posts into correspond support apertures and coupled thereto. According to one embodiment of the disclosure, the posts of the posterior cover may be formed of a solid material and inserted into corresponding apertures formed within the posterior panel. In response to the heat staking process, the posts are deformed to create a head portion that prevents removal of the post from being extracted from the aperture without removal of the head portion. The posts operate as (i) spacers to provide architectural stability by maintaining substantially constant side openings for adjustment of the telescopic lateral panels inward and outward from the first chamber and (ii) stops to preclude complete removal of the telescopic lateral panels from the first chamber.

The front surface of the pulley cover includes posts that are coupled to support apertures formed within the posterior cover. These posts may be applied in accordance with the heat staking process described above, or in the alternative, may be applied to be removable from these apertures (e.g., threaded, apertures with generally the same diameter as the posts for snug fitting, etc.) to allow an orthotist access to the pulley subsystem positioned under the pulley cover. These posts also operate as spacers, which provide architectural stability and allow movement of the pulley bases of the pulley subsystem unencumbered by forces being applied to the posterior cover and/or the pulley cover that would constrict a depth of the second chamber.

The pulley bases are interconnected by cords, where the tightening of the pulley cords (i.e., pulling on the handle at the end of the pulley cords) causes both pulley bases to transverse inwardly towards each other along a guide channel that is formed on a rear surface of the posterior cover to operate as part of the second chamber. During an inward traversal, the orthopedic belt is tightened. During such tightening, the pulley bases move inwardly towards each other, which causes the length of each belt member attached to a pulley bases along with lateral panel to which the belt member is attached, to reduce in size extending from the first and second chambers. Stated differently, during tightening, both the lateral panels and their corresponding belt members are drawn back into the first chamber and second chamber, respectively.

Conversely, by relaxing of the pulley cords (or loosening of the orthosis fastening subsystem), the pulley bases are moved outwardly towards pulley stops that are integrated as part of on the guide channel. Located on opposite sides of the pulley base, the flange members are positioned to engage with the stops when the belt and lateral panel extend from the first and second chambers to a prescribed length set during a belt adjustment process that may occur during the donning of the orthopedic brace.

I. Terminology

In the following description, certain terminology is used to describe aspects of the invention. For example, the term "member" may be construed as a structural component of an orthopedic brace. In certain situations, a member may include a component covered by soft goods such as one or more textiles, one or more fabrics (woven fabrics and/or non-woven fabrics), leathers, and/or another covering material. These soft goods may feature "loop" type fasteners or other variants to which a "hook" type fastener may be attached or may feature a hook-type fastener for attachment to a loop-type fastener. In other situations, the member may be soft goods attached to another structural component of the orthopedic brace such as a textile or fabric sewn to form together such as a knit textile with pockets in which the structural component(s) can be positioned within the pocket (s).

The term "chamber" is a partially enclosed housing, namely a structure having partially enclosed perimeter except for one or more openings, such as at least two openings at opposite sides along the periphery for example. As a result, a partially enclosed chamber operates as a structure that is configured to secure, maintain and protect orthosis fastening subsystem components.

The term "attach" and other tenses of the term (attached, attaching, etc.) may be construed as physically connecting a first member to a second member. A "fastener" may be construed as any physical component that is used to attach different members together. An illustrative example of different types of fasteners and fastening techniques may include, but are not limited or restricted to snaps, buttons, clasps, buckles, adhesives, sewing, heat sealing (or melting), gluing, knitting, or other physical coupling techniques such as a hook and loop connection.

The terms "rigid" or "rigidity" with respect to a member or portion of a member may be construed as the member being configured to at least partially resist bending or deformation. According to this definition, different lengths of a given structure and composition can be rigid at a shorter length, and flexible at a longer length. As used herein, the term "rigid" with respect to a member or portion of a member may be construed as the member could be permanently deformed or broken if bent or twisted by at least 90°. Examples of a rigid member may include, but is not limited or restricted to the posterior panel or the extension panel, where the telescopic lateral panels are rigid, but are flexible to support placement into a concave-shape without breaking.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

II. General Architecture

Referring to FIG. 1, a perspective rear view of an exemplary embodiment of a posterior bracing system 110 deployed as part of an orthopedic brace 100 is shown. Herein, the posterior bracing system 110 features a posterior panel 120 that is oriented, when worn, to generally reside or is substantially in parallel with a frontal plane of the patient. As shown, a filler 115 (padding) may be inserted adjacent to an anterior surface of the posterior panel 120. The posterior panel 120 provides support along a thoracic and lumbar regions of the patient's spine.

As further shown, the posterior bracing system 110 further features a plurality of structural members layered onto the posterior panel 120 to create a plurality of chambers therebetween. These structural members may include, but are not limited or restricted to a posterior cover 140 and a pulley cover 160. The posterior cover 140 is coupled to a curved, midsection region 125 of the posterior panel 120. This midsection region 125 is generally concave in shape to conform with the thoracic and lumbar regions of a patient's spine. One or more slotted openings 130 are positioned on each side (left 126, right 128) of the midsection region 125 to lessen lateral rigidity of the posterior panel 120 to allow for lateral and anterior movement of the sides of the posterior panel 120 when worn. As also shown, a top area 132 of the posterior panel 120 features locking slots 134 for retention of extension panels (not shown) and strap slots 136 for retention of an attachment strap (not shown).

The pulley cover 160 is coupled to the posterior cover 140, namely at a midsection region 145 of the posterior cover 140. This midsection region 145 of the posterior cover 140 features a recessed area (not shown), which is shaped to maintain a pulley subsystem 150 including a plurality of pulley bases $\mathbf{152_1}$-$\mathbf{152_2}$. Each of the pulley bases $\mathbf{152_1}$ or $\mathbf{152_2}$ includes (i) a base member $\mathbf{154_1}$ or $\mathbf{154_2}$ with a plurality of pulley members (not shown) positioned in a staggered orientation and interconnected with a designated pulley cord $\mathbf{180_1}$ or $\mathbf{180_2}$ with a handle 1851 or $\mathbf{185_2}$, and (ii) a belt slot $\mathbf{156_1}$ or $\mathbf{156_2}$ positioned on an outer lateral edge of the pulley base member $\mathbf{154_1}$ or $\mathbf{154_2}$. Each pulley cord $\mathbf{180_1}$ or $\mathbf{180_2}$ is threaded through cord passage apertures 1701 or $\mathbf{170_2}$ that reside within the same traversal plane. The pulley cover 160 is smaller in size (e.g., width and height) than the posterior cover 140 so as to overlay the recessed area of the posterior cover 140 so that the pulley cover 160 refrains from covering a top cover region 158 and a bottom cover region 159 of the posterior cover 140.

Referring to FIG. 2A, an exploded view of an exemplary embodiment of the posterior bracing system 110 of FIG. 1 is shown. Herein, the posterior bracing system 110 features the posterior panel 120, the posterior cover 140 and the pulley cover 160 as shown in FIG. 1. The liner 115 is positioned anterior to a front surface 200 of the posterior panel 120. Furthermore, a plurality of lateral panels 210 are made of a rigid or semi-rigid material such as any type of hardened, flexible plastic (e.g., sheet of polyethylene, polycarbonate, etc.) and are positioned within a first chamber 280 (see also FIG. 2B) formed between a rear surface 205 of the posterior panel 120 and a front surface 220 of the posterior cover 140 (and adjacent to another liner 117). The pulley subsystem 150 is positioned within a second chamber 290 (see also FIG. 2B), which is formed between a rear surface 225 of the posterior cover 140 and a front (anterior) surface 230 of the pulley cover 160. Adjustable belt members 240 are attached to the belt slots $\mathbf{156_1}$-$\mathbf{156_2}$ formed within the pulley bases $\mathbf{152_1}$-$\mathbf{152_2}$.

Figure 4A:
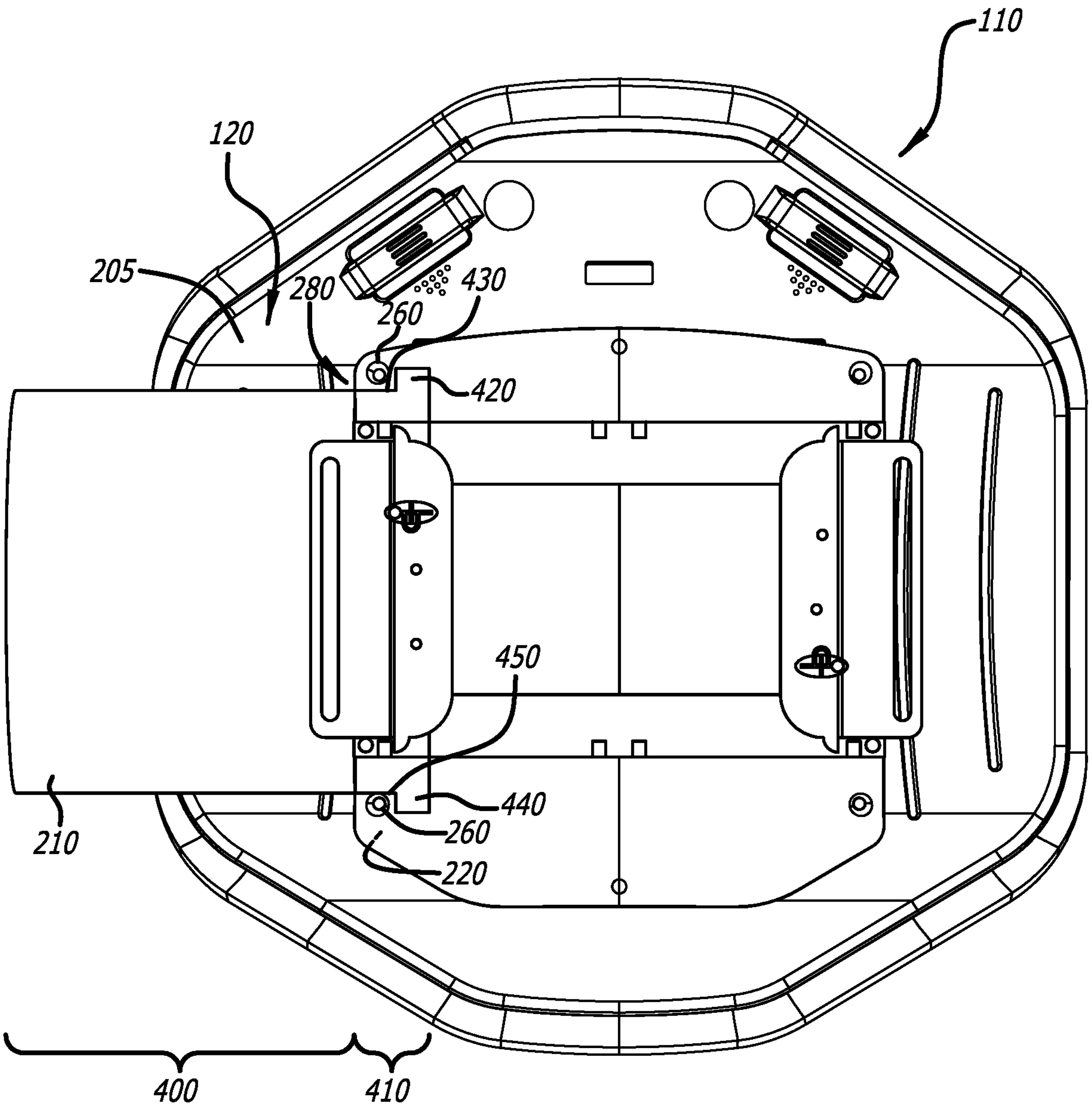
FIG. 4A is a top-down planar view of the brace adjustment system featuring telescopic panels and a belt deployed between the posterior panel and the posterior cover of FIG. 2.
Figure 4B:
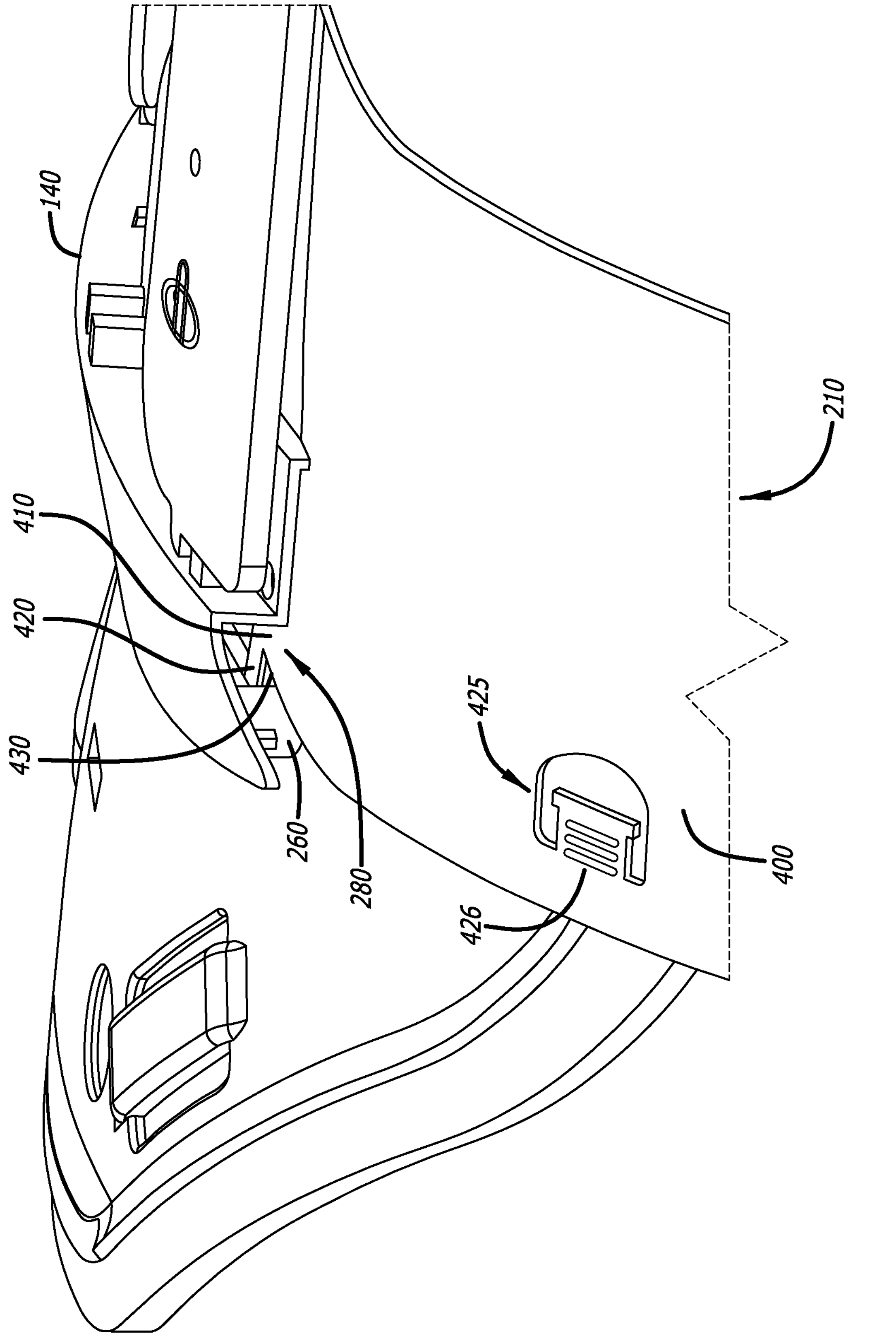
FIG. 4B is a cut-away view of the brace adjustment system illustrating stops including a first stop type to preclude continued extension of the telescopic lateral panel from the first chamber formed between the posterior panel and the posterior cover.

More specifically, the front surface 220 of the posterior cover 140 includes a plurality of posts 260, which are coupled to the posterior panel 120, where such coupling may be realized by insertion of the posts 260 into correspond support apertures 265 within the posterior panel 120 and permanently fused thereto (e.g., coupled together by a heat staking process). The posts 260 operate as (i) spacers to provide structural integrity by maintaining substantially constant width to side openings formed within the first chamber 280 (see FIG. 2B) for adjustment of the telescopic lateral panels 210 inward and outward from the first chamber 280 and (ii) stops to preclude complete removal of the lateral panels 210 from the first chamber 280 by tab portions of the lateral panels 210 engaging with the posts 260 as shown in FIGS. 4A-4B and described below.

Herein, according to one embodiment of the disclosure, the telescopic lateral panels 210 provide support by lessening circumferential pressure and helping with stabilizing the spinal system from bending sideways (coronal plane). The rigid, plastic lateral panels 210 may extend from sacrococcygeal junction area and terminate just inferior to the scapular spine. In combination with lateral panels associated with an anterior bracing system (not shown) that extend from symphysis pubis to the sternal notch, soft liner, the lateral panels 210 assist in restricting gross trunk motion in sagittal, coronal, and transverse planes as well as provides lateral strength.

Additionally, the pulley cover 160 features the front surface 230 that also includes a plurality of posts 270. However, the posts 270 may be removably coupled to support apertures 275 formed within the posterior cover 140. The posts 270 operate as spacers, which provide the structural integrity to resist substantial narrowing or closure of side openings formed within the second chamber 290 in response to forces exerted on the pulley cover 160 in an anterior direction D1 or forces exerted on the posterior cover 140 in a posterior direction D2. This allows the belt slots $156_1$-$156_2$ located on the pulley bases $152_1$-$152_2$ to be exposed from the second chamber 290 and unencumbered during usage.

Referring to both FIGS. 2A-2B, the pulley bases $152_1$-$152_2$ are interconnected by the pulley cords $180_1$-$180_2$ extending from a back (posterior) surface 235 of the pulley cover 160, where the tightening of one or both of the pulley cords $180_1$-$180_2$ (i.e., pulling on the handle 1851 at the end of the pulley cord $180_1$) causes both pulley bases $152_1$-$152_2$ to traverse inwardly towards each other along a guide channel 222 formed on the rear surface 225 of the posterior cover 140. During traversal, one or more of the orthopedic belt members 240 is tightened. During such tightening, the pulley bases $152_1$-$152_2$ move inwardly towards each other, which cause the length of each of the lateral panels (e.g., lateral panel 210) and its corresponding belt member 240, respectively extending from the first and second chambers 280 and 290, to be reduced as each belt member 240 is coupled to its corresponding lateral panel via hook and loop fastener, a loop connection attached to a surface of the belt member 240 and fed through a slot in the lateral panel 210 for attachment to a complementary fastener on the lateral panel. As a result, during adjustment, both the lateral panel 210 and its corresponding belt member 240 may be moved along a first lateral direction (L1) 292 away from the first and second chambers 280 and 290. However, during tightening, the lateral panel 210 and its corresponding belt member 240 is drawn back into the first chamber 280 and second chamber 290 in accordance with a second lateral direction (L2) 294, as described in more detail below.

Figure 3A:
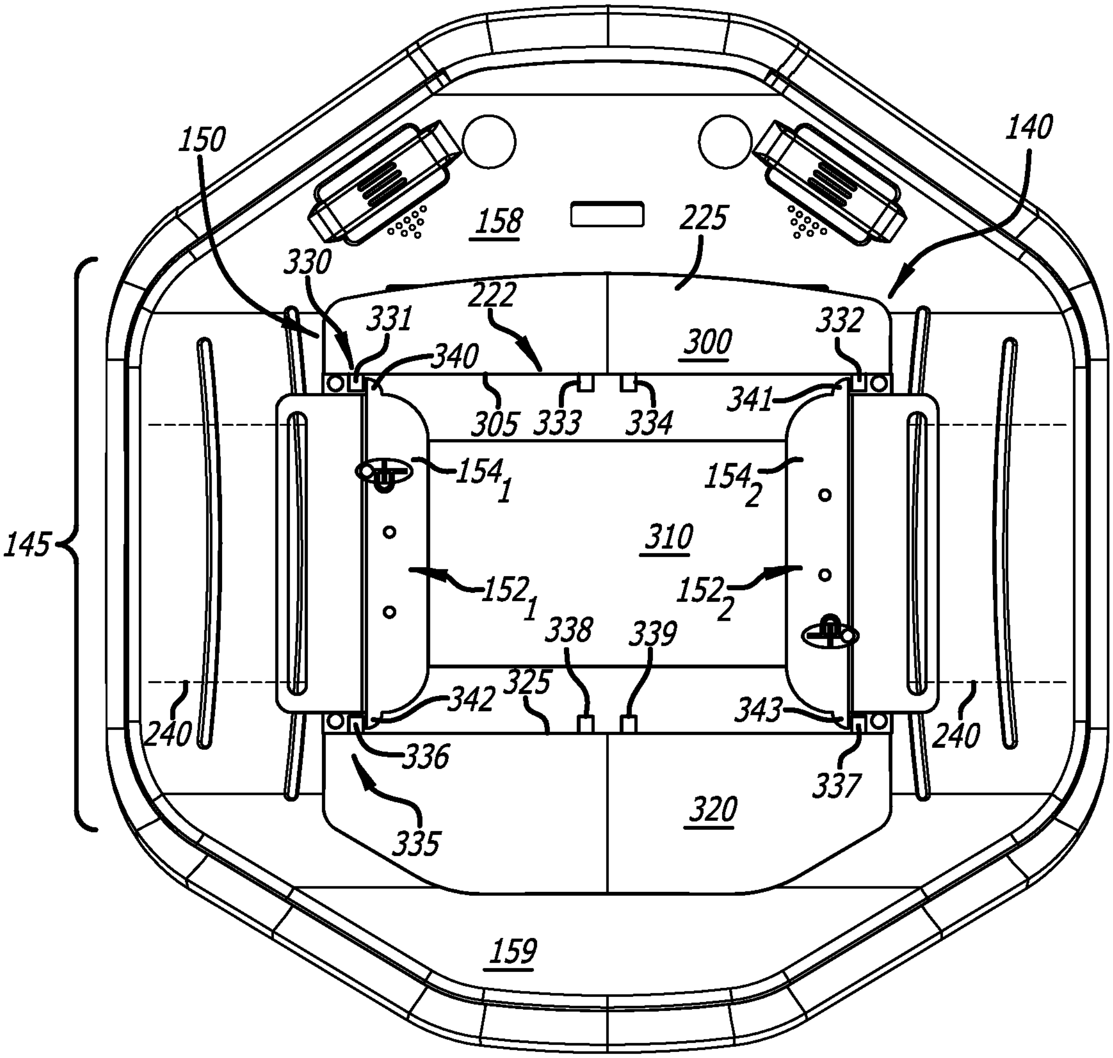
FIG. 3A is a top-down planar view of an exemplary embodiment of the pulley subsystem implemented with a guide channel formed within the posterior cover of FIG. 2A.

Referring to FIG. 3A, a top-down planar view of an exemplary embodiment of the pulley subsystem 150 implemented with the guide channel 222 formed within the posterior cover 140 is shown. Illustrating a rear surface 225 of the posterior cover 140, the posterior cover 140 is structured with the midsection cover region 145 integrated with and interposed between the top cover region 158 and the bottom cover region 159. The midsection cover region 145 features the guide channel 222 formed by a first guide member 300, a second guide member 310, and a third guide member 320.

As further shown in FIG. 3A, a first set (two or more) of pulley stops 330 are positioned along a side surface 305 of the first guide member 300 and a second set of pulley stops 335 are positioned along a side surface 325 of the third guide member 320. The first and second sets of pulley stops 330 and 335 are positioned to prevent the pulley bases $152_1$ and $152_2$ from being accidentally slid and removed from the guide channel 222. More specifically, each pulley base member $154_1$ and $154_2$ features a first flange 340 and 341, which is positioned to engage with one of the first set of pulley stops 330 (e.g., pulley stops 331 and 332) when each belt member 240 is set to a prescribed size and is fully extended from the second chamber 290. Similarly, each pulley base member $154_1$ and $154_2$ features a second flange 342 and 343, which is positioned to engage with one of the second set of pulley stops 335 (e.g., pulley stops 336 and 337) when each belt member 240 is set to a prescribed size and is fully extended from the second chamber 290. As an optional feature, besides pulley stops 331-332 and 336-337, the first and second set of pulley stops 330 and 335 may include pulley stops 333-334 and 338-339 to prevent further inward movement of the pulley bases $152_1$ and $152_2$ beyond a prescribed location.

Figure 3B:
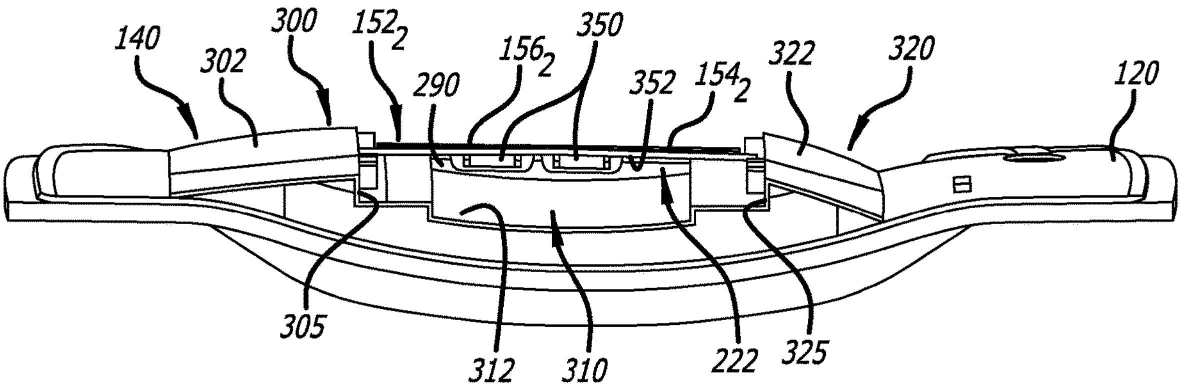
FIG. 3B is a side view of an exemplary embodiment of the posterior cover illustrating a second chamber formed, at least in part, by the guide channel.

Referring now to FIG. 3B, a side view of an exemplary embodiment of the posterior cover 140 is shown, which illustrates the second chamber 290 formed, at least in part, by the guide channel 222. Herein, given that the posterior panel 120 is shaped to conform with the contours of the thoracic and lumbar back regions, a rear-facing surface 312 of the second guide member 310 is positioned below a rear-facing surface 302 of the first guide member 300 and a rear-facing surface 322 of the third guide member 320. The rear-facing surface 302 of the first guide member 300 is generally orthogonal to the side surface 305 of the first guide member 300, and the rear-facing surface 322 of the third guide member 320 is generally orthogonal to the side surface 325 of the third guide member 320. This construction provide sufficient clearance for pulleys 350 mounted on a front-facing surface 352 of the pulley base member (e.g., pulley base member $154_2$ of the pulley base $152_2$), as the pulley base $152_2$ slides along the first and third guide members 300 and 320 in response to forces applied to the belt slot $156_2$ and/or forces applied via the pulleys 350.

Figure 3C:
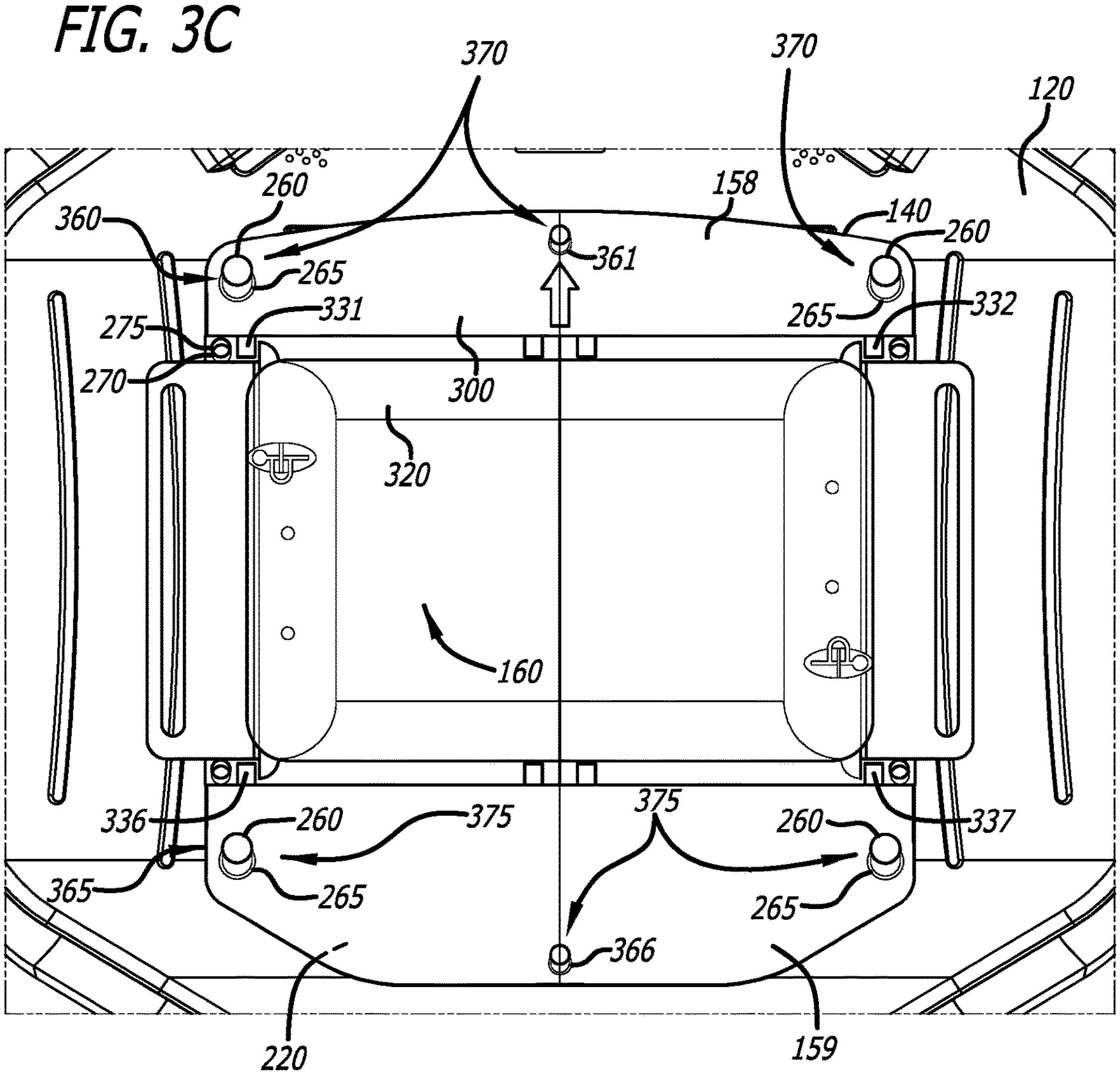
FIG. 3C is a cut-way view of an exemplary embodiment of support apertures implemented within the posterior panel of FIG. 2A.

Referring to FIG. 3C, a cut-way view of an exemplary embodiment of support apertures 265 implemented within the posterior panel 120 of FIG. 2A is shown. Herein, as shown in FIGS. 3B-3C, the plurality of support apertures 265 are positioned to correspond to the plurality of posts 260 extending from the front surface 220 of the posterior cover 140. As shown, a first set of support apertures 360 are positioned to engage with a first set of posts 370 extending from a top cover region 158 of the posterior cover 140. Additionally, a second set of support apertures 365 are positioned to engage with a second set of posts 375 extending from a bottom cover region 159 of the posterior cover 140. According to one embodiment, except for an optional central support aperture 361, a remainder of the first set of support apertures 360 may be coplanar. Similarly, except for a central support aperture 366, a remainder of the second set of support apertures 365 may be coplanar. Support apertures 275 for engagement with posts 270 associated with the pulley cover 160 (see FIG. 2A) may be positioned along the first guide member 300 and the second guide member 320 in closer proximity to the pulley stops 331-332 and 336-337 than the support apertures 265.

Figure 3D:
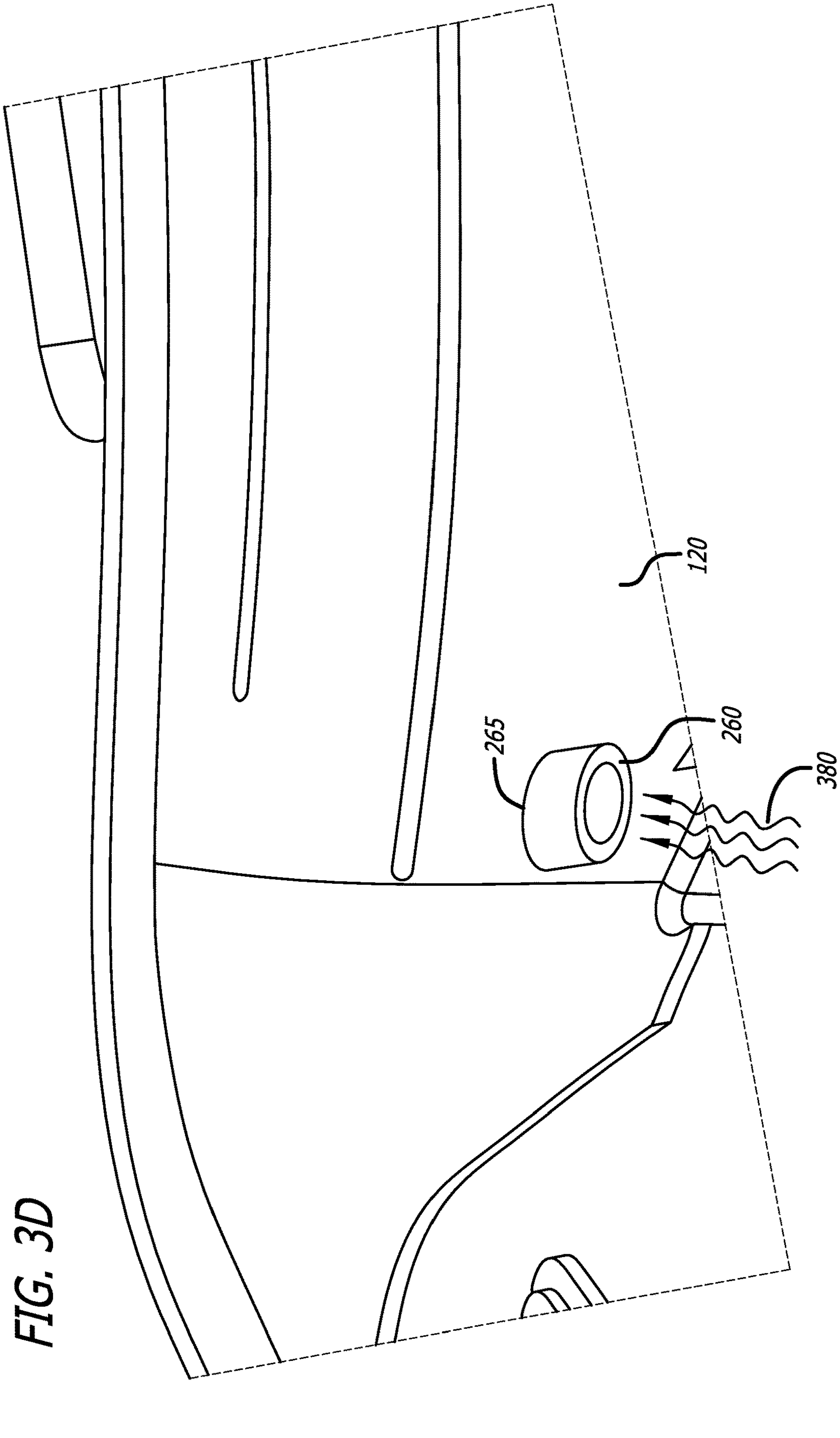
FIG. 3D is a perspective view of an exemplary embodiment of a heat staking process, where a post and support aperture operate as a coupling point between the posterior panel and the posterior cover of FIG. 2A.

Referring to FIG. 3D, a perspective view of an exemplary embodiment of a heat skating process is shown, where the post 260 and support aperture 265 operate as a coupling point between the posterior panel 120 and the posterior cover 140 as well as a reinforcement member. According to this embodiment of the disclosure, the post 260 of the posterior cover 140 may be inserted into a corresponding support aperture 265 formed within the posterior panel 120 and coupled together. For example, the post 260 and the support aperture 265 may be coupled together through a heat staking process 380. In particular, after insertion of the post 260 within the support aperture 265, a prescribed amount of heat is applied to the post 260. This heat causes the material associated with the post 260 to slightly melt to form a head portion (dome) with a diameter greater that the aperture 265 so that, upon cooling, the post 260 cannot be removed from the support aperture 265 without disfigurement or elimination of the head portion.

Referring to FIG. 4A, a top-down planar view of the posterior bracing system 110, featuring the telescopic lateral panel 210 deployed between the first chamber 280 formed between the posterior panel 120 and the posterior cover 140, is shown. According to one embodiment of the disclosure, the telescopic lateral panel 210 includes a main panel region 400 and a retention panel region 410. As shown, the main panel region 400 corresponds to the portion of the lateral panel 210 that may be removed from the first chamber 280, namely an enclosure formed between the rear surface 205 of the posterior panel 120 and the front surface 220 of the posterior cover 140. The amount of the main panel region 400 removed from the first chamber 280 is dependent on a size (large (L), medium (M), small (S), or variations thereof such as XL, 2XL, XS, etc.) selected for the belt strap member 240 attached to the lateral panel 210 as illustrated in FIGS. 6A-6E.

According to one embodiment of the disclosure, the main panel region 400 of the telescopic lateral panel 210 may include a buckle attachment aperture 425 that is sized to receive a buckle associated with a support strap (not shown) positioned under an axilla of the wearer. When the support strap is inserted therethrough, the buckle attachment aperture 425 features a buckle retention appendage 426, which is flexible and applies a force against an inserted buckle to retain the buckle at least partially within the buckle attachment aperture 425. As a result, the buckle attachment aperture 425 assists in retention of the buckle and its support strap to remain under and away from the axilla of the wearer. This avoids unwanted movement of the strap when the orthopedic brace 100 is worn.

As further shown in FIGS. 4A-4B, the retention panel region 410 corresponds to a minimum portion of the lateral panel 210 that is configured to always remain within the first chamber 280. According to this embodiment of the disclosure, the retention panel region 410 includes a first tab portion 420 extending from its edge 430. The first tab portion 420 (and the lateral panel 210) is positioned to engage with the post 260 of the posterior cover 140, operating as a "stop" for the lateral panel 210, when the lateral panel 210 has been extended to a size in which the main panel region 400 is fully removed from the first chamber 280. The first tab portion 420 prevents the lateral panel 210 from being accidentally removed from the first chamber 280 upon engaging with the post 260. Besides the first tab portion 420, as shown in FIG. 4A, a second tab portion 440 may be positioned to extend from an edge 450 of the retention panel region 410 and engage with another post 260 of the posterior cover 140 when the main panel region 400 is fully removed from the first chamber 280.

Figure 4C:
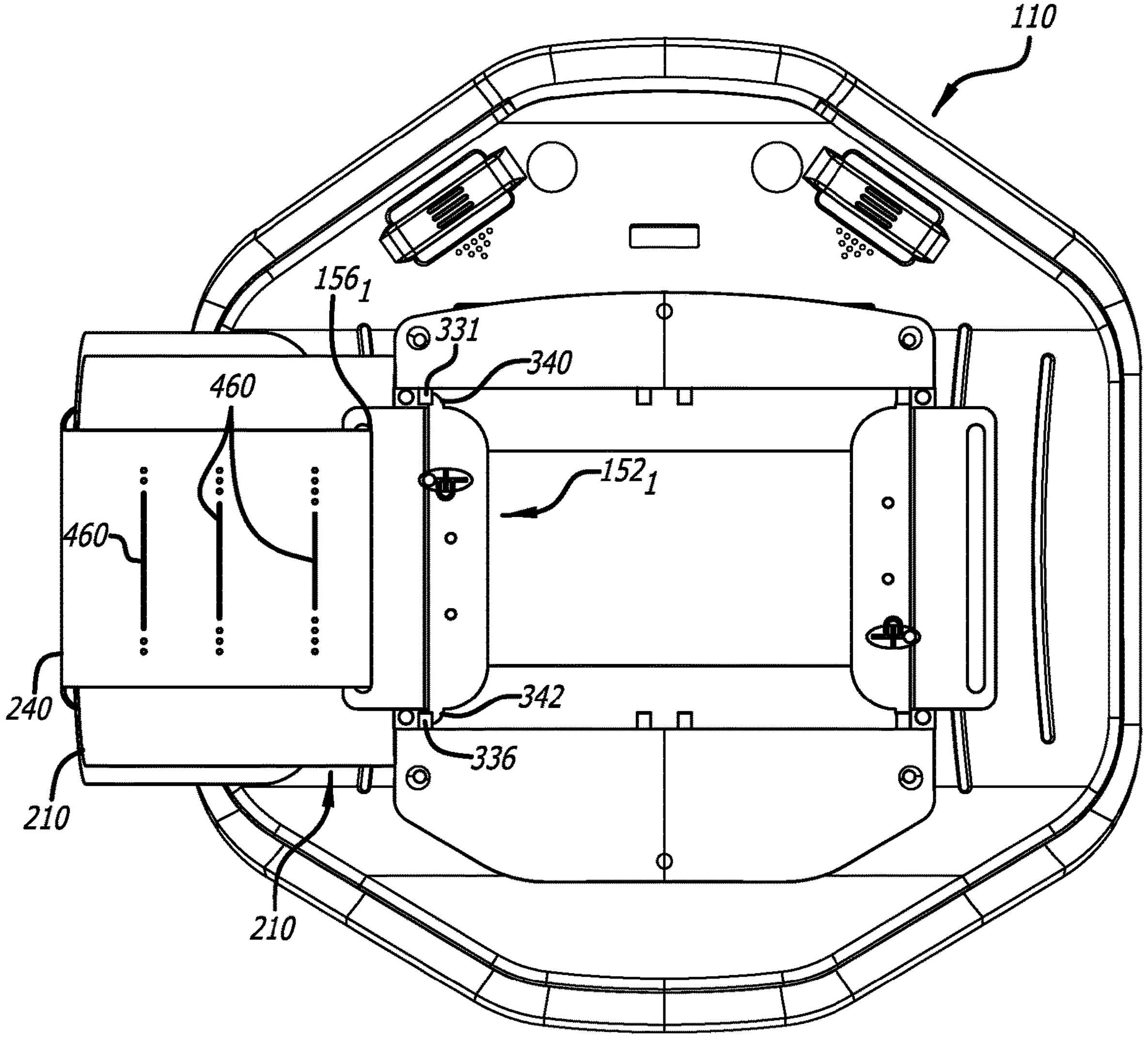
FIG. 4C is a top-down planar view of the posterior bracing system, featuring the telescopic lateral panel operating with the adjustable belt member.

Referring now to FIG. 4C, a top-down planar view of the posterior bracing system 110, featuring the telescopic lateral panel 210 operating with the adjustable belt member 240, is shown. Herein, the belt member 240 is attached to the pulley base $\mathbf{152_1}$ via the belt slot $\mathbf{156_1}$. The belt member 240 may be sized based on indicia 460 placed on the belt member 240 being aligned with a portion of the pulley base $\mathbf{152_1}$, such as a belt slot $\mathbf{156_1}$. Herein, however, the belt member 240 has been sized to a maximum length as denoted by the first and second flanges 340 and 342 are engaging pulley stops 331 and 336. The lateral panel 210 and belt member 240 are coupled together and moved laterally and anteriorly for coupling with an anterior bracing system (not shown).

Figure 5A:
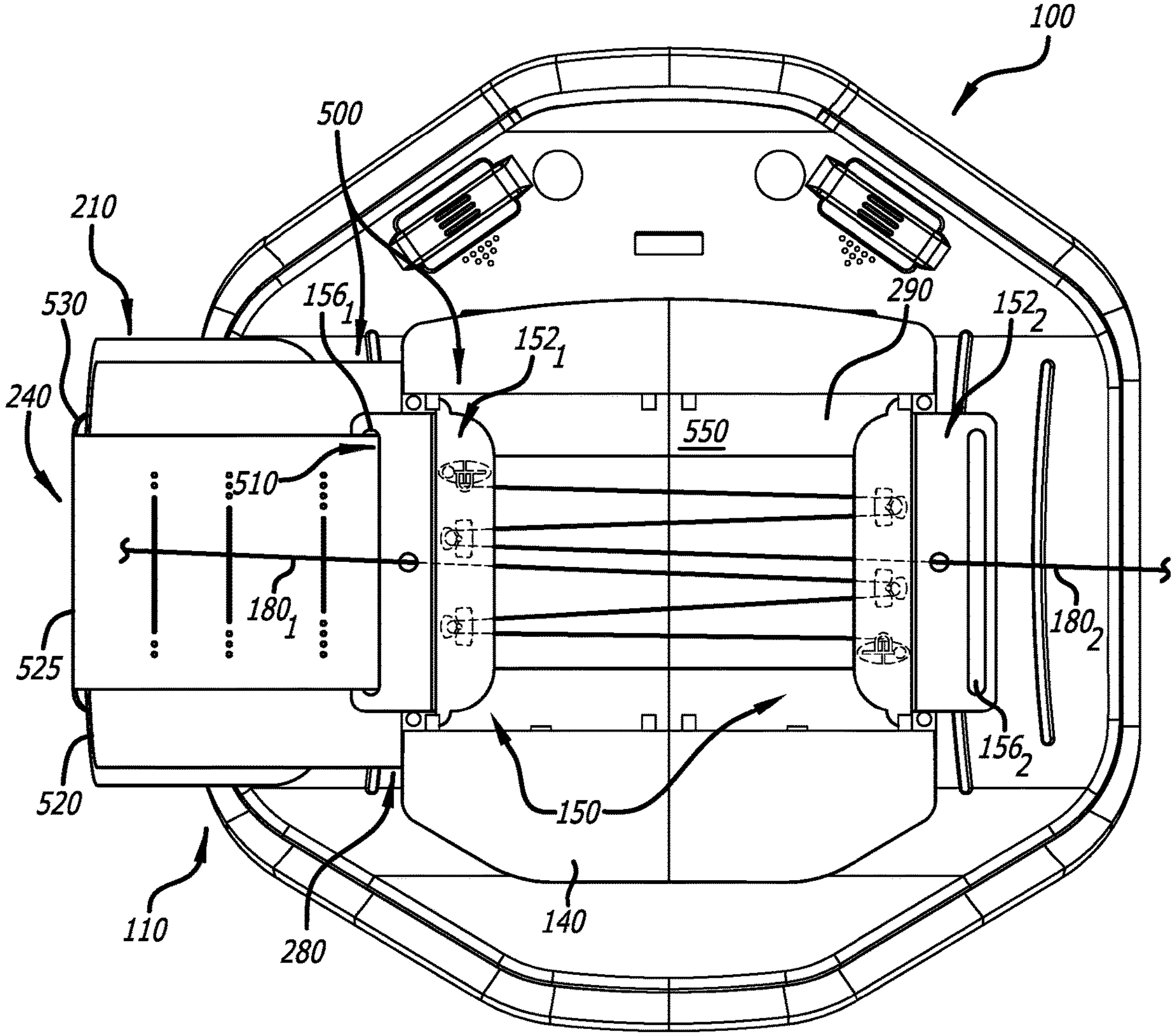
FIG. 5A is an exemplary embodiment of an orthosis fastening subsystem deployed within the orthopedic brace of FIG. 1.

Referring now to FIG. 5A, an exemplary embodiment of an orthosis fastening subsystem 500 deployed within the orthopedic brace 100 is shown. Implemented as components of the posterior bracing system 110, the orthosis fastening subsystem 500 features the pulley subsystem 150, the telescopic lateral panels 210 (e.g., a first lateral panel 520 as shown), and the belt members 240 (e.g., a first belt member 525 as shown), which operate together for sizing and attachment of the orthopedic brace 100 to a patient. The first telescopic lateral panel 520 slidably extends from the first chamber 280 formed under the posterior cover 140 in a direction opposite to a direction of extension of a second telescopic lateral panel (not shown). Additionally, a first end 510 of the first belt member 525 is anchored to the belt slot $\mathbf{156_1}$ of the first pulley base $\mathbf{152_1}$ while a first end of the second belt member (not shown) would be anchored to the belt slot $\mathbf{156_2}$ of the second pulley base $\mathbf{152_2}$.

Figure 5B:
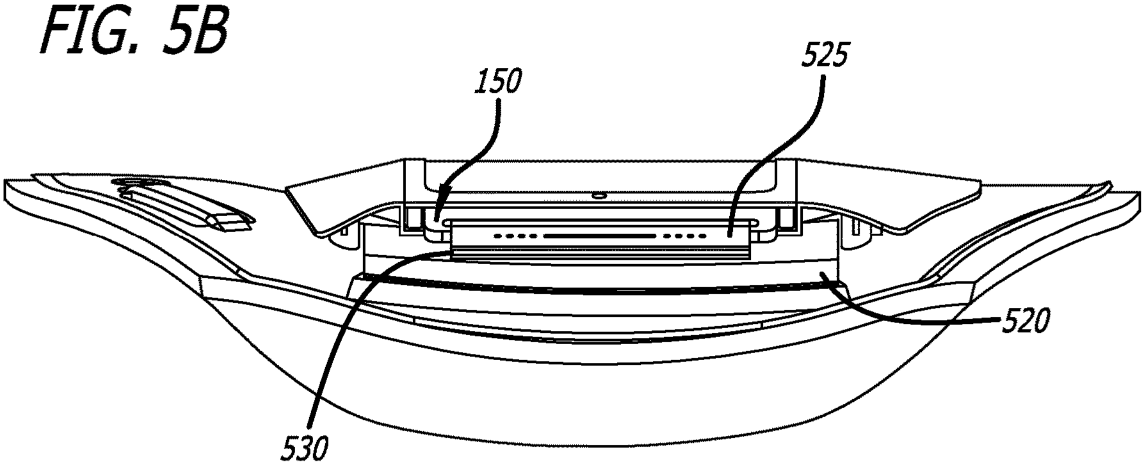
FIG. 5B is a side view of an exemplary embodiment of posterior bracing system featuring the pulley subsystem of FIG. 5A.

As further shown in FIGS. 5A-5B, the pulley subsystem 150 includes the first pulley base $\mathbf{152_1}$ and the second pulley base $\mathbf{152_2}$ coupled together through the pulley cords $\mathbf{180_1}$ and $\mathbf{180_2}$. Although not shown, the pulleys mounted under the pulley bases $\mathbf{152_1}$-$\mathbf{152_2}$ apply tension and cause inward movement (toward a central area 550 of the second chamber 290) of (i) the first belt member 525 when the pulley cord $\mathbf{180_2}$ is pulled away in an anterior and/or lateral direction and (ii) the second belt member (not shown) when the pulley cord $\mathbf{180_1}$ is pulled away in an anterior and/or lateral direction. Additionally, given that a portion of the first belt member 525, proximate to the a second end 530 of the first belt member 525, is attached to the first lateral panel 520 as shown in FIG. 5B, such as through complementary loop and hook fasteners for example, inward movement of the first belt member 525 causes complementary interior movement of the first lateral panel 520 and vice versa. The same adjustment scheme would be applicable to the second lateral panel (not shown). This enables easier donning of the orthopedic brace without log-rolling the patient for customized re-fitting of the posterior lateral panels.

Figure 5C:
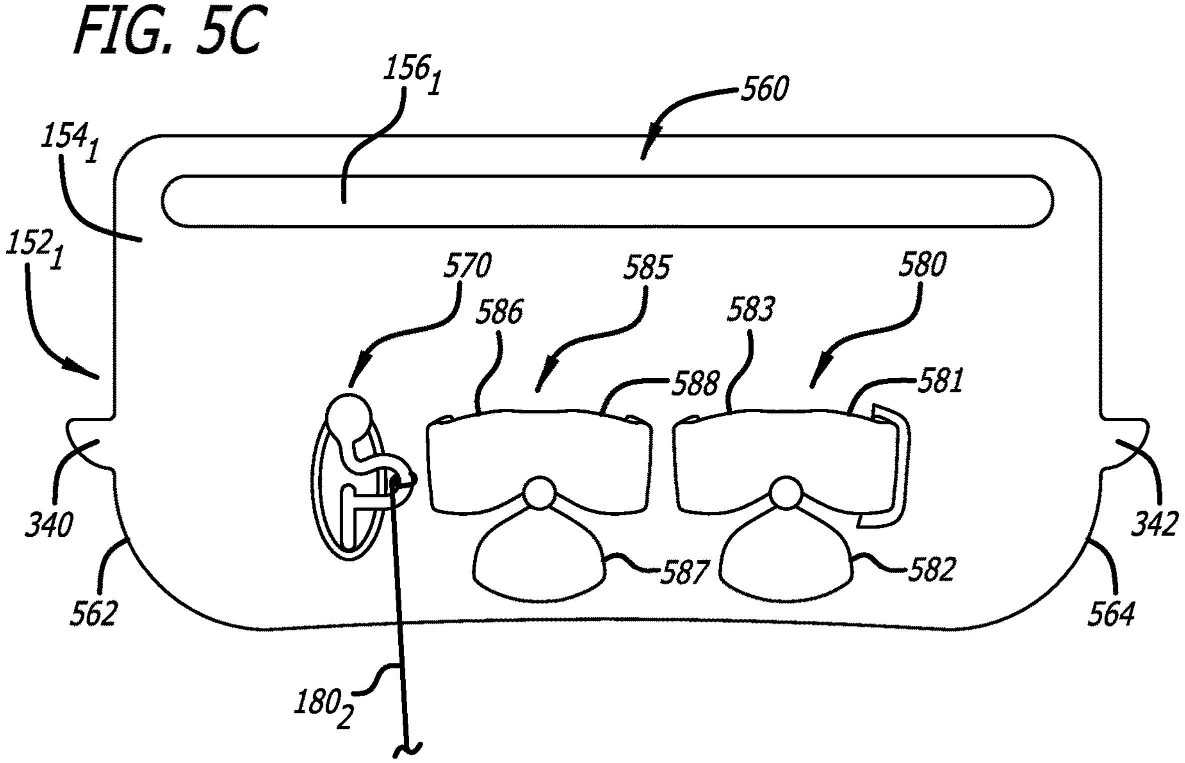
FIG. 5C is a top-down planar view of an exemplary embodiment of the pulley base of FIG. 5A.

Referring to FIG. 5C, a top-down planar view of an exemplary embodiment of a pulley base (e.g., pulley base $\mathbf{152_1}$) of FIG. 5A is shown. Herein, the pulley base $\mathbf{152_1}$ includes the base member $\mathbf{154_1}$ featuring (i) the belt slot $\mathbf{156_1}$ positioned proximate to a first outer lateral edge 560 of the base member $\mathbf{154_1}$, (ii) the first flange 340 positioned on a second outer lateral edge 562 of the base member $\mathbf{154_1}$, and (iii) the second flange 342 positioned on a third outer lateral edge 564 of the base member $\mathbf{154_1}$. Herein, both the second and third outer lateral edges 562 and 564 are generally orthogonal to first outer lateral edge 560. The second and third outer lateral edges 562 and 564 are positioned on opposite sides of the base member $\mathbf{154_1}$.

Mounted on the base member $\mathbf{154_1}$, a first pulley cord attachment member 570 is configured to securely attach an end 182 of the second pulley cord $\mathbf{180_2}$ to the pulley base $\mathbf{152_1}$. The second pulley cord $\mathbf{180_2}$ is provided from the first pulley cord attachment member 570 to the second pulley base $\mathbf{152_2}$ as shown in FIG. 5A. Further mounted on the base member $\mathbf{154_1}$, a first pulley 580 is configured to receive the second pulley cord $\mathbf{180_2}$ from a pulley mounted on the second pulley base $\mathbf{152_2}$, where the second pulley cord $\mathbf{180_2}$ is threaded through an input port 581, wound around a first pulley wheel 582, and threaded through an output port 583 towards cord passage apertures $\mathbf{170_2}$. A second pulley 585 is configured to receive the first pulley cord $\mathbf{180_1}$ from the second pulley base $\mathbf{152_2}$, where the first pulley cord $\mathbf{180_1}$ is threaded through an input port 586, wound around a second pulley wheel 587, and threaded through an output port 588 for return to another pulley of the second pulley base $152_2$.

Figure 5D:
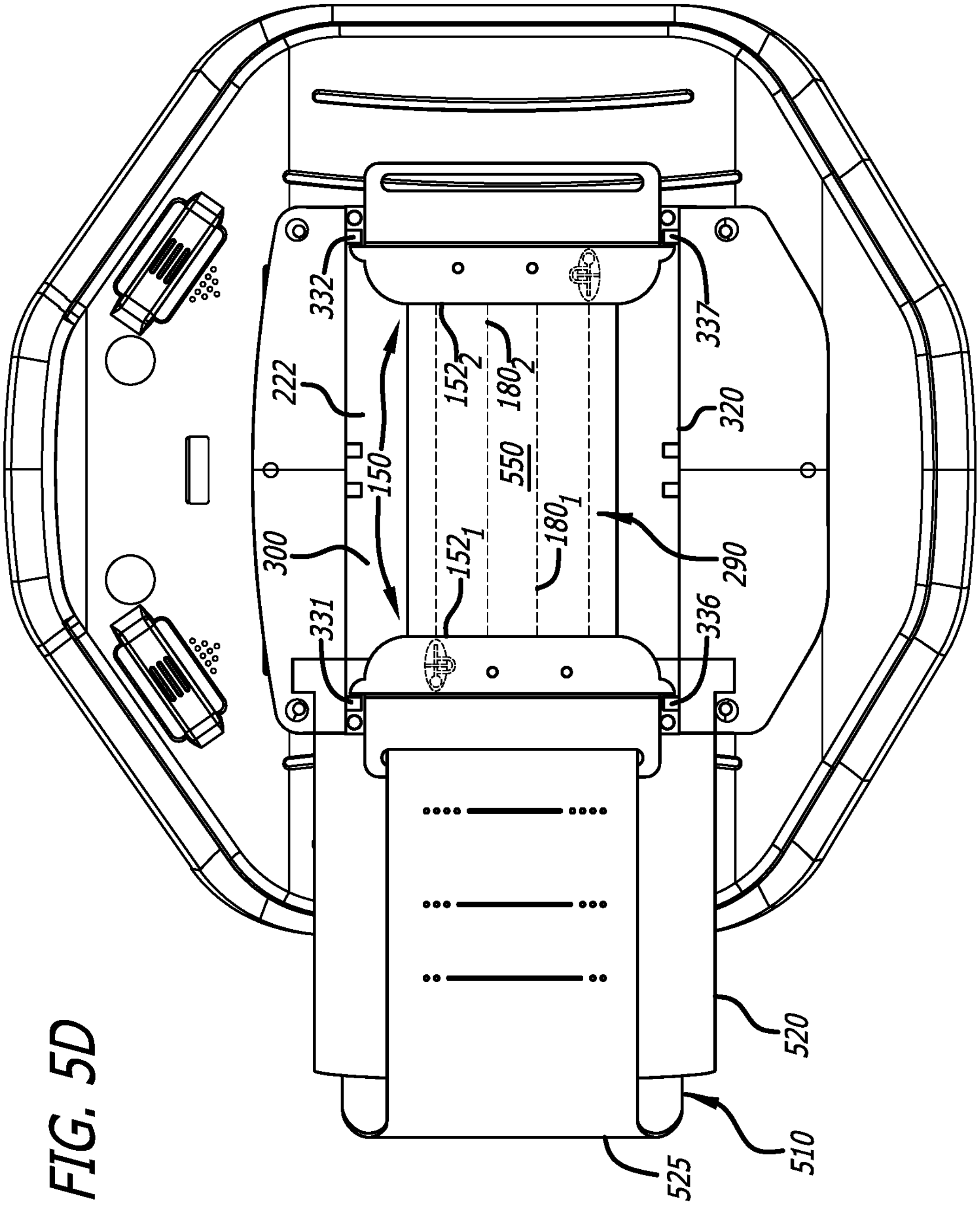
FIG. 5D is a top-down planar view of an exemplary embodiment of the pulley subsystem operating in a first state.
Figure 5E:
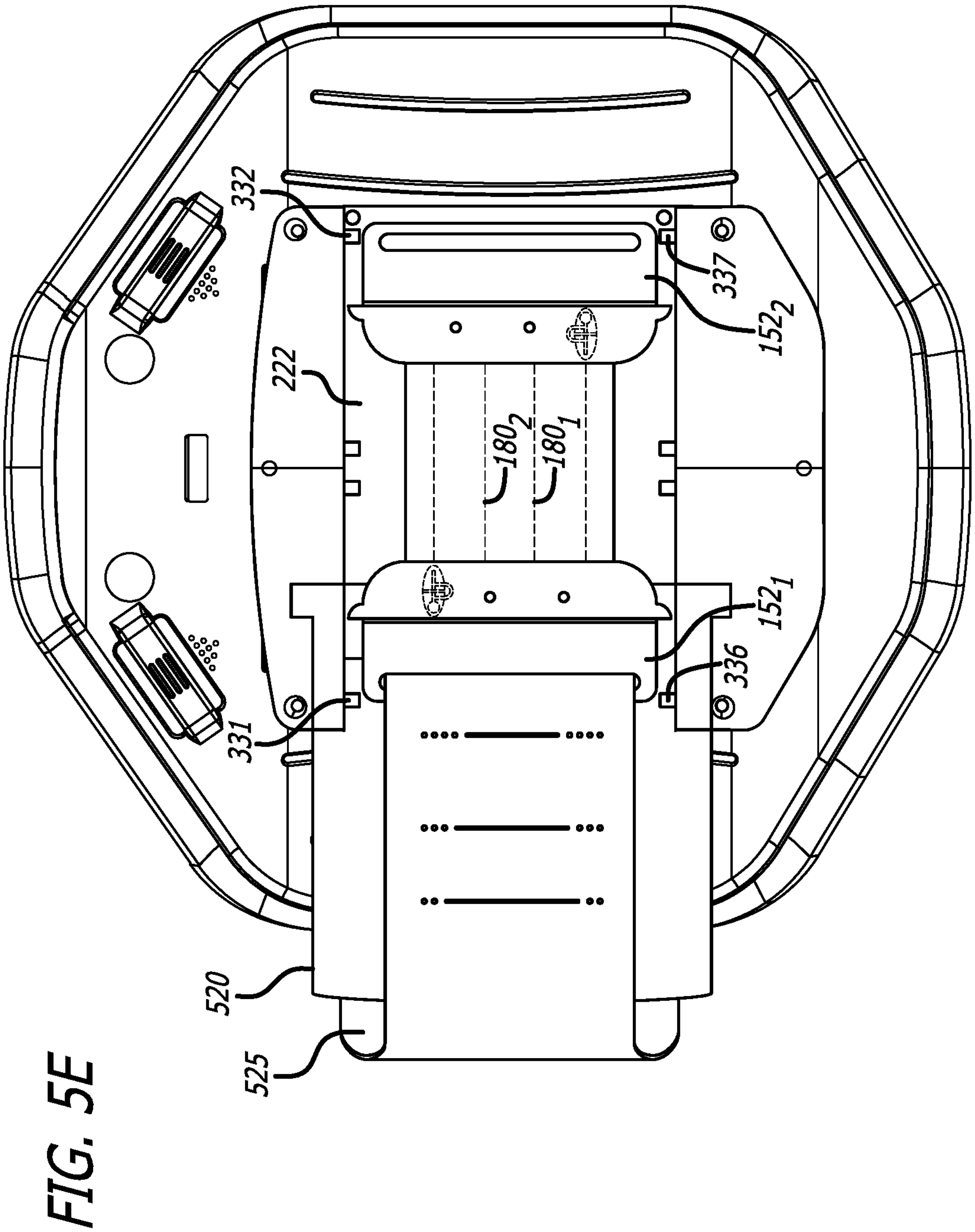
FIG. 5E is a top-down planar view of an exemplary embodiment of the pulley subsystem operating in a second state in response to a tightening operation in which the telescopic lateral panel and the belt member partially return into the first and second chambers.

As shown in FIG. 5D, after setting of the sizing of the belt members 240 and attachment to the lateral panels 210, the pulley bases $152_1$-$152_2$ of the pulley subsystem 150 are positioned in a first state. In the first state, the pulley bases $152_1$-$152_2$ may be located closer to the pulley stops 331-332 and 336-337 than the central area 550 of the second chamber 290. In response to tightening of pulley cord(s) $180_1$ and/or $180_2$, as shown in FIG. 5E, the pulley bases $152_1$-$152_2$ traverse along the guide channel 222, in particular the first and third guide members 300 and 320, towards the central area 550 of the second chamber 290. The pulley bases $152_1$-$152_2$ are non-stationary as these pulley bases $152_1$ and $152_2$ push their corresponding lateral panel/belt member combinations outwardly from the first and second chambers during initial sizing as well as pull their corresponding lateral panel/belt member combinations into the first and second chambers 280 and 290 during tightening. For example, the pulley base $152_1$ is configured to push its corresponding lateral panel/belt member combinations 520/525 outwardly from the first and second chambers during initial sizing as well as pull the corresponding lateral panel/belt member combinations 520/525 into the first and second chambers 280 and 290 during tightening Referring now to FIG. 6A-6B, exemplary embodiments of an internal sizing of a second belt member 600 (e.g., opposite to belt member 525 of FIG. 5A) is shown, with subsequent sizing of the telescopic lateral panel 620 (e.g., opposite to lateral panel 520 of FIG. 5A). Herein, the second belt member 540 includes a first set of indicia 610 that identifies different belt sizes (large, medium, small, etc.) when oriented with a selected portion of the pulley base $152_2$. For example, as an illustrated embodiment, the indicia 610 may include a plurality of indicia elements 615 each corresponding to a different belt size so that the second belt member 600 is sized accordingly. More specifically, a selected indicia element 612 may be oriented with a selected portion of the pulley base $152_2$ (e.g., within the belt slot $156_2$ of the pulley base $152_2$), and thereafter, a first fastener 625 (e.g., loop and hook fastener) at a first end 622 of the second belt member 600 is coupled to a second fastener 626 (e.g., complementary loop and hook fastener) located along an interior surface 628 of the second belt member 600 so as to wrap the second belt member 600 around the belt slot $156_2$ and the point of connection facing inward. As a result, the second belt member 600 is placed in a size corresponding to the selected indicia element 612.

Figure 6A:
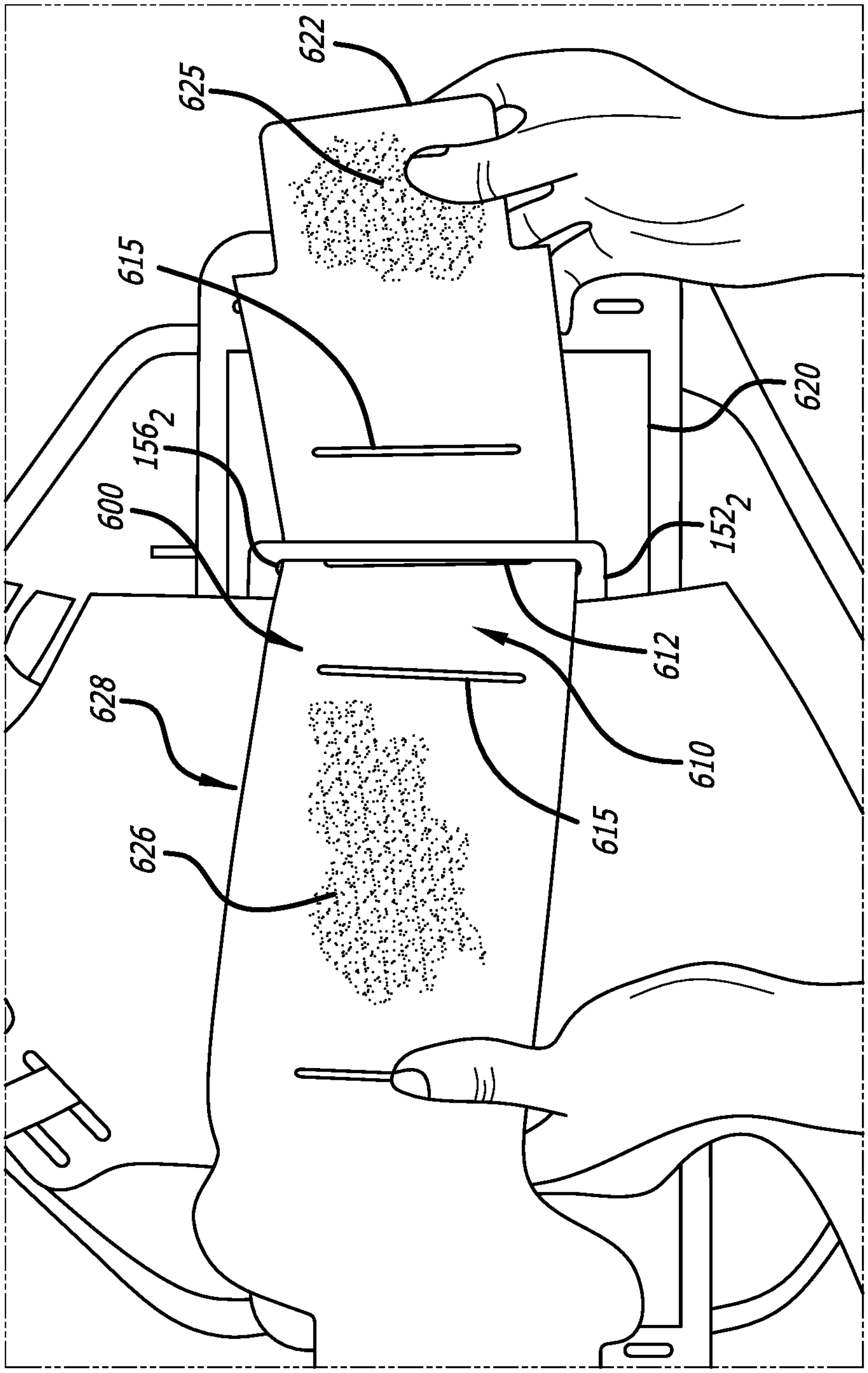
FIG. 6A-6B are exemplary embodiments of an internal sizing of the belt and subsequent sizing of the telescopic lateral panel deployed within the posterior bracing system of FIG. 2A.
Figure 6B:
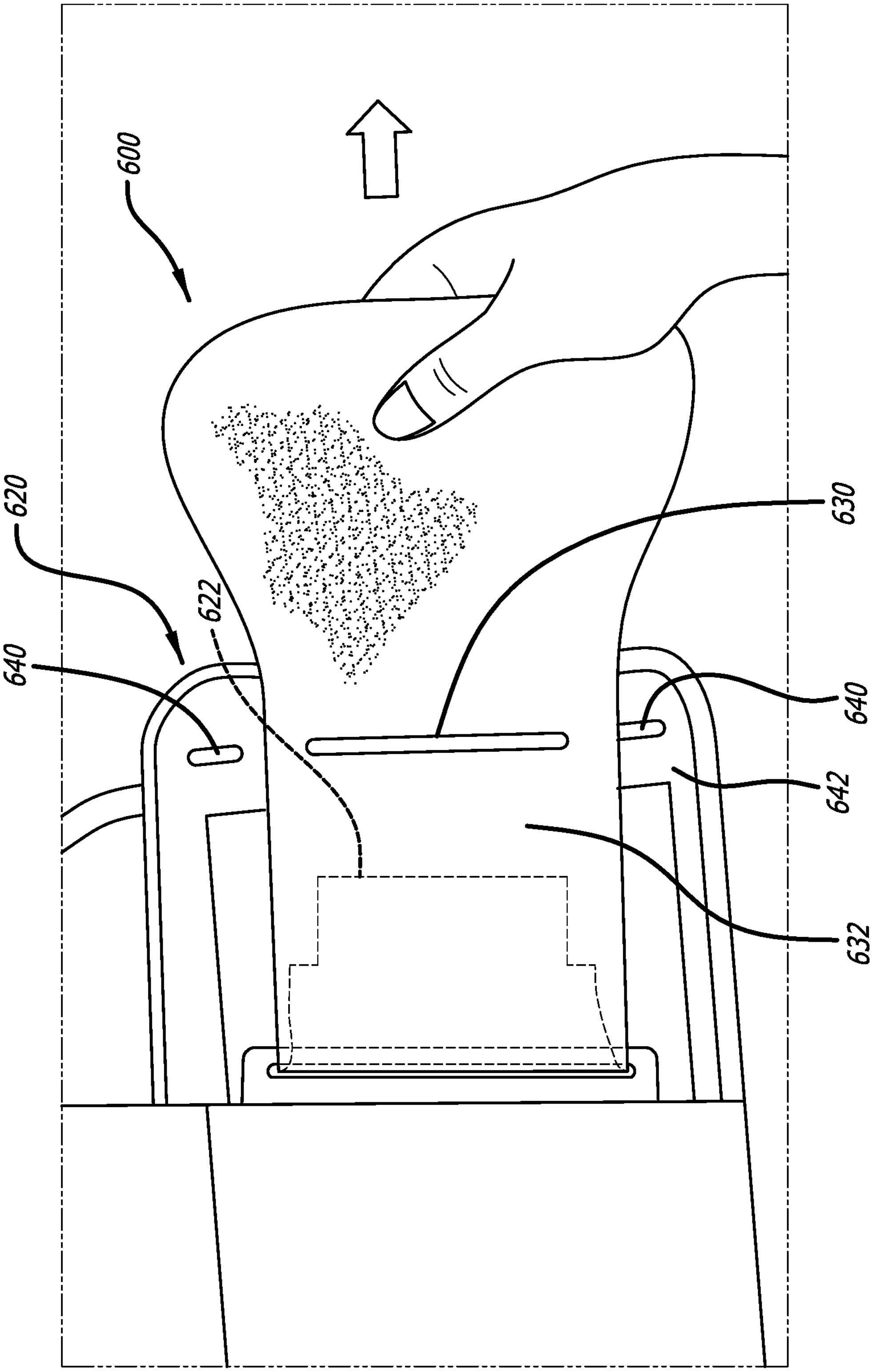

After the second belt member 600 has been sized, as shown in FIG. 6B, indicia 630 located on its exterior surface 632 is aligned with indicia 640 located on a rear-facing surface 642 of the telescopic lateral panel 620 so that the telescopic lateral panel 620 is set to an identical size. Hence, the second belt member 600 restricts side extension of the telescopic lateral panel 620 to comfort with the sizing of the second belt member 600. It is contemplated that an exteriorly sized belt 600 may be semi-permanently attached to the lateral panel 620 so that we can reduce sizing needs by the orthotist. As a result, the orthotist or clinician would not need to align the belt to the indicia 640 on the lateral panel 620.

Figure 6C:
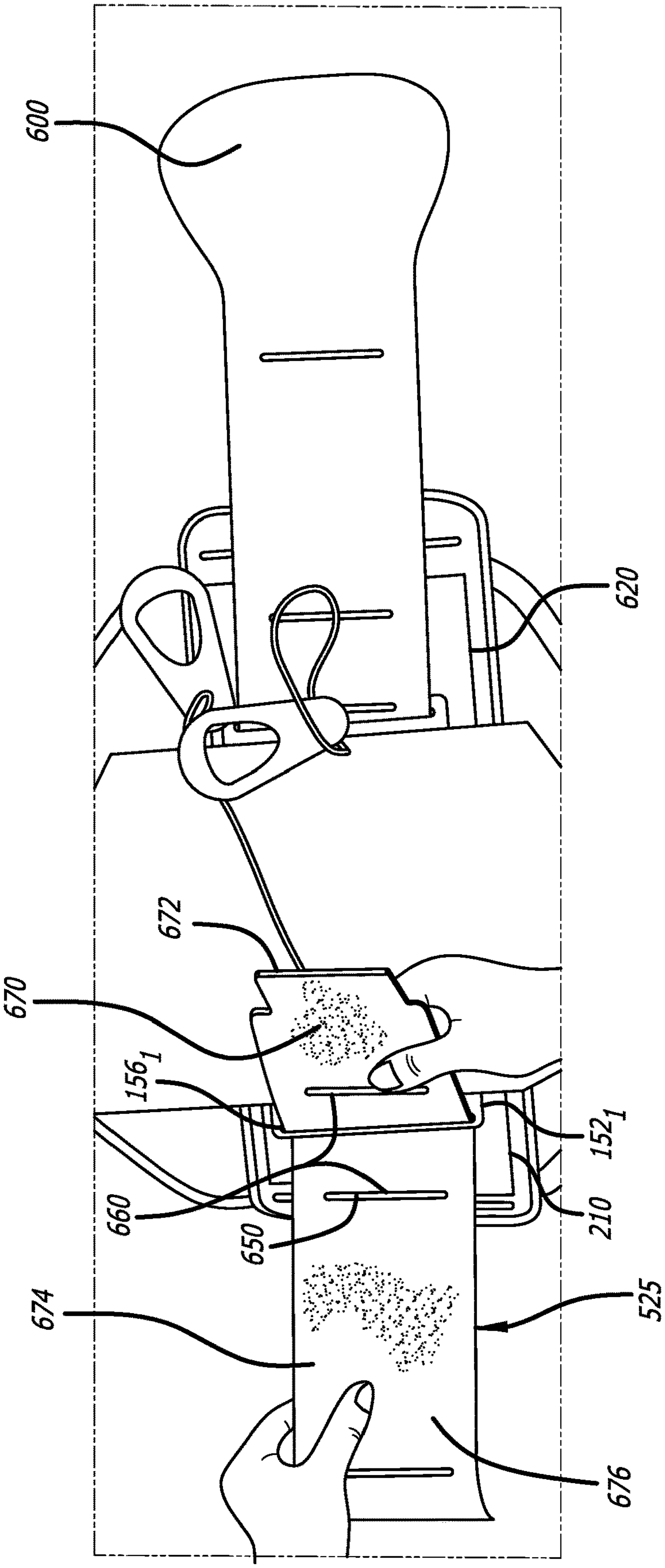
FIG. 6C-6D are exemplary embodiments of an external sizing of the belt and subsequent sizing of the telescopic lateral panel deployed within the posterior bracing system of FIG. 2A.
Figure 6D:
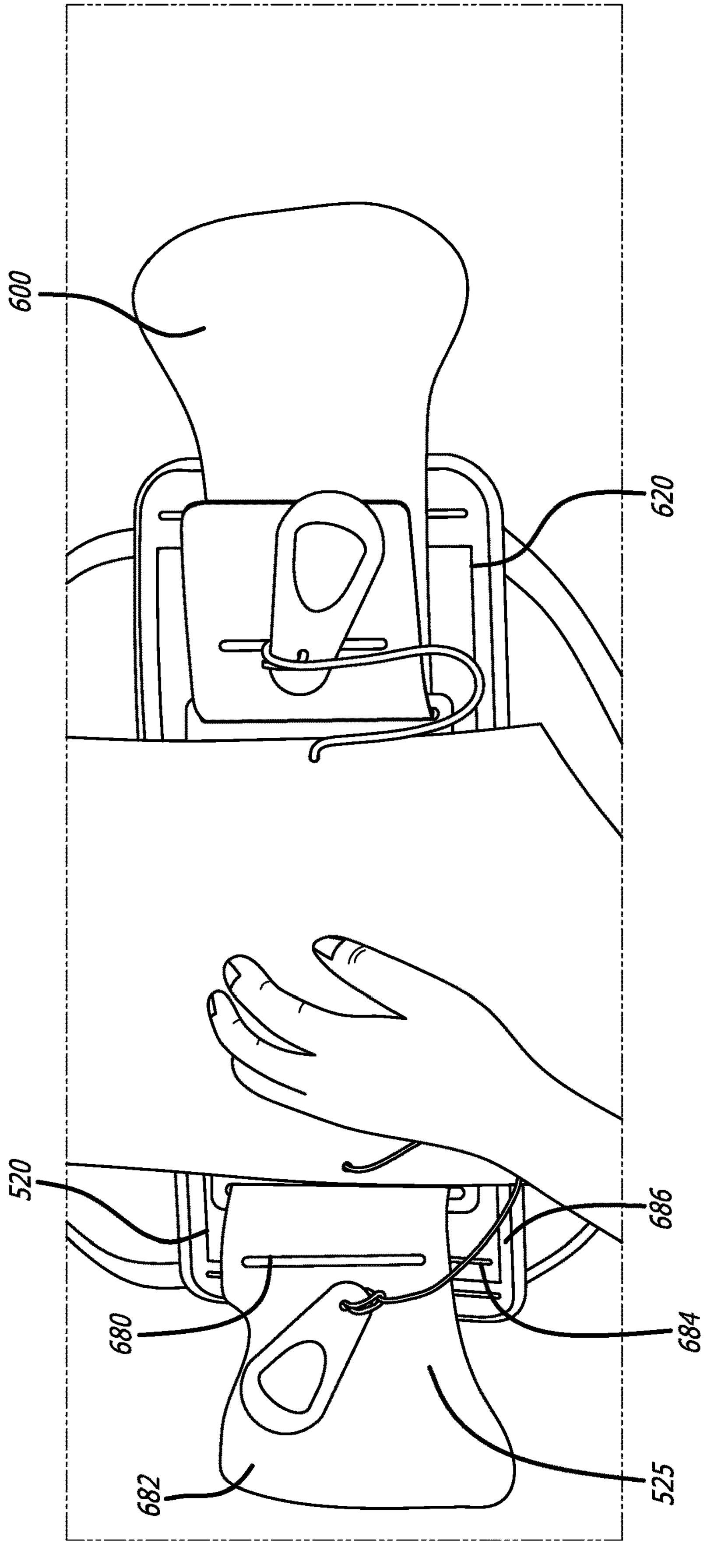

Referring to FIG. 6C-6D, exemplary embodiments of an external sizing of a belt member (e.g., the first belt member 525 of FIG. 5A) is shown, with subsequent sizing of the telescopic lateral panel 520. Herein, the first belt member 525 includes a first set of indicia 650 that identifies different belt sizes (large, medium, small, etc.) when oriented with a selected portion of the pulley base $152_1$. For example, as an illustrated embodiment and similar to the internal sizing of a belt member shown in FIGS. 6A-6B, the indicia 650 may include a plurality of indicia elements 660 each corresponding to a different belt size so that the first belt member 530 is sized accordingly. More specifically, a selected indicia element may be oriented with a selected portion of the pulley base $152_2$ (e.g., within the belt slot $156_1$ of the pulley base $152_1$), and thereafter, a first fastener 670 (e.g., loop and hook fastener) at a first end 672 of the first belt member 525 is coupled to a second fastener 674 (e.g., complementary loop and hook fastener) located along an outer surface 676 of the first belt member 525 so as to wrap the first belt member 525 around the belt slot $156_1$ and the point of connection facing outward. As a result, the first belt member 525 is placed in a size corresponding to the selected indicia element.

After the first belt member 525 has been sized, as shown in FIG. 6D, indicia 680 located on its exterior surface 682 is aligned with indicia 684 located on a rear-facing surface 686 of the telescopic lateral panel 520 so that the telescopic lateral panel 520 is set to an identical size. Hence, the first belt member 525 restricts side extension of the telescopic lateral panel 520 to comfort with the sizing of the first belt member 525.

Figure 6E:
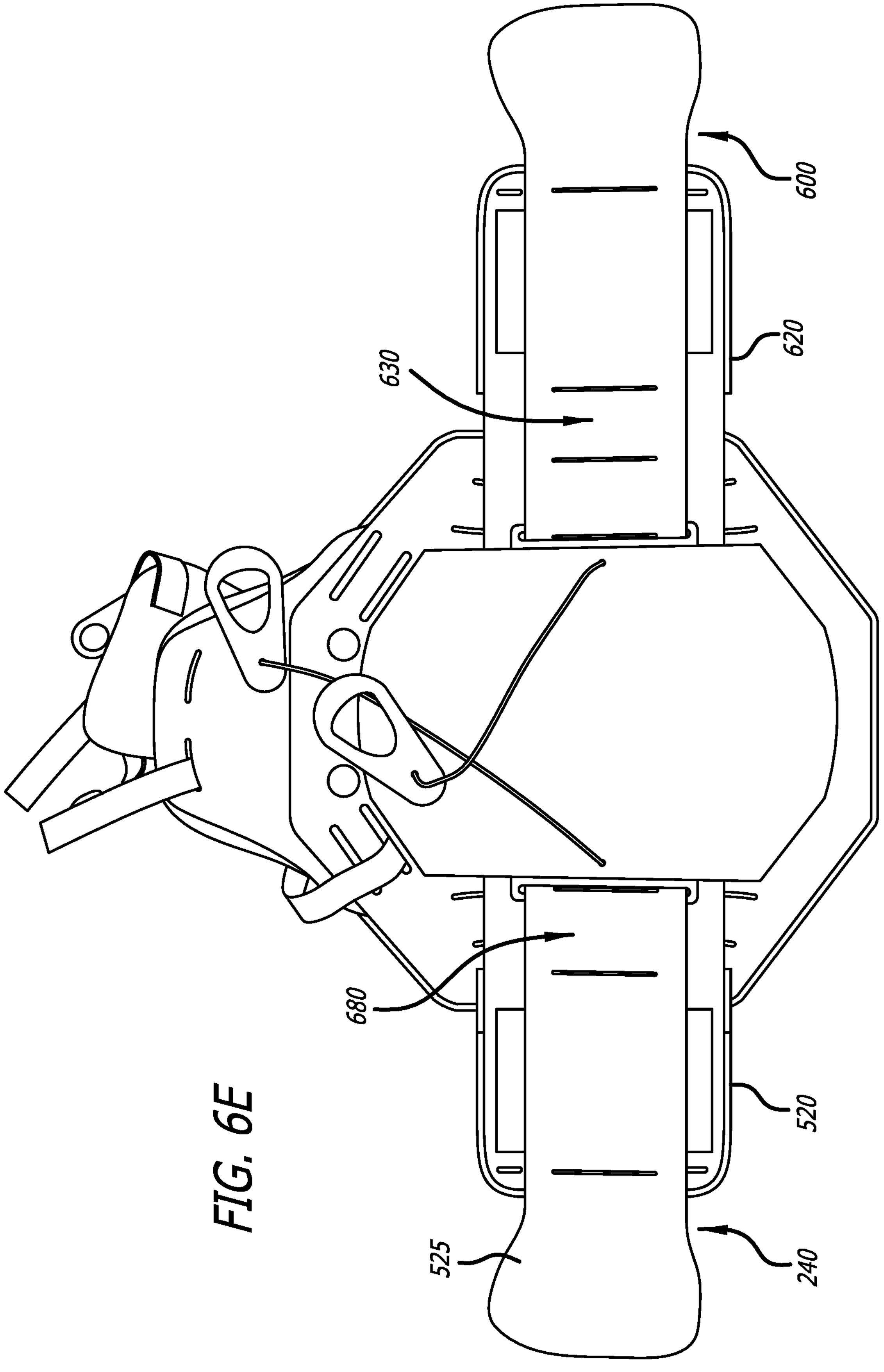
FIG. 6E is an exemplary embodiment of the orthosis fastening system being adjusted to illustrate different lateral panel and belt member combinations with different size settings conducted in accordance with different belt sizing processes as illustrated in FIGS. 6A-6D.

As a result, as shown in FIG. 6E as an illustrative example, the first belt member 525 has been sized in accordance with an external sizing process into a "medium" sizing. The second belt member 600 has been sized in accordance with an internal sizing process into a "large" sizing. The indicia 680 on the first belt member 525 is aligned with slots (or indicia) on the first telescopic lateral panel 520. The indicia 630 on the second belt member 600 is aligned with slots (or indicia) on the second telescopic lateral panel 620. As a result, both lateral panels 520 and 620 are sized consistent with their corresponding belt members 525 and 600, and thus, the second telescopic lateral panel 620 (sized to large) extends further outside the first chamber than the first telescopic lateral panel 520 (sized to medium).

In the foregoing description, the invention is described with reference to specific exemplary embodiments thereof. For example, the telescopic lateral panels and adjustable belt member combination, operating with a pulley subsystem, may be deployed within an LSO orthopedic brace with an architecture different than the orthopedic brace described above. Hence, it will be evident that certain components may be deployed within different types of orthopedic braces and various modifications and changes may be made thereto without departing from the broader spirit and scope of the invention as set forth in the appended claims.

What is claimed is:

1. A posterior bracing system deployed as part of an orthopedic brace, comprising:

a posterior panel;

a posterior cover coupled to the posterior panel, the posterior cover being configured to create a first chamber partially formed by an anterior facing surface of the posterior cover and a posterior facing surface of the posterior panel including a guide channel formed on the posterior facing surface of the posterior panel; and a pulley cover coupled to the posterior cover to create a second chamber partially formed by an anterior facing surface of the pulley cover and a posterior facing surface of the posterior cover, the second chamber to house a pulley subsystem including a plurality of pulley bases, wherein the guide channel enables lateral movement of (i) a first pulley base of the plurality of pulley bases between a first opening within the second chamber and a central area of the second chamber and (ii) a second pulley base of the plurality of pulley bases between a second opening within the second chamber and the central area of the second chamber, and wherein the first pulley base of the plurality of pulley bases includes (i) a first flange extending toward a first edge of the guide channel including at least a first stop that, upon the first flange coming into contact with the first stop, prevents further lateral movement of the first pulley base towards the first opening and (ii) a second flange extending towards a second edge of the guide channel, the second edge of the guide channel including at least a second stop positioned in alignment with the first stop so that, upon the first flange coming into contact with the first stop and the second flange coming into contact with the second stop, further lateral movement of the first pulley base towards the first opening is prevented.

2. The posterior bracing system of claim 1, wherein the first chamber is configured to house a plurality of telescopic panels each arranged to extend laterally outward of the first chamber.

3. The posterior bracing system of claim 2, wherein the first opening of the second chamber being positioned on an opposite side of the second chamber as the second opening.

4. The posterior bracing system of claim 2, wherein a first belt member is attached to the first pulley base and a second belt member is attached to the second pulley base.

5. The posterior bracing system of claim 4, wherein the first belt member associated with the first pulley base is attached to a first telescopic panel of the plurality of telescopic panels so that the first belt member moves concurrently with the first telescopic panel.

6. The posterior bracing system of claim 5, wherein the first belt member is extended from the second chamber when the first telescopic panel is extended from the first chamber and the first belt member retreats within the second chamber when the first telescopic panel retreats within the first chamber.

7. The posterior bracing system of claim 2, wherein each of the plurality of telescopic panels includes a main panel region and a retention panel region, the main panel region of a first telescopic panel corresponding to a first portion of the first telescopic panel removable from the first chamber and the retention panel region corresponds to a second portion of the first telescopic panel remaining within the first chamber.

8. The posterior bracing system of claim 7, wherein the retention panel region of the first telescopic panel includes a first tab portion and a second tab portion that contact posts of the posterior cover operating as stops to prevent complete removal of the first telescopic panel from the first chamber.

9. The posterior bracing system of claim 1, wherein the first pulley base includes a first belt slot to which a first belt member is attached and the second pulley base includes a second belt slot to which a second belt member is attached, each of the first belt member and the second belt member includes indicia for internal or external sizing of the first belt member and the second belt member.

10. The posterior bracing system of claim 9, wherein the first belt member associated with the first pulley base is attached to a first telescopic panel, the first telescopic panel including indicia for aligning with the indicia for sizing the first belt member to set a degree of extension and retraction of the first telescopic panel from the first chamber.

11. The posterior bracing system of claim 7, wherein the pulley cover includes a first aperture to receive a first pulley cord to control movement of the first pulley base by causing retraction of a first belt member into the second chamber and retraction of the first telescopic panel of the plurality of telescopic panels into the first chamber, where the first aperture retains that the first pulley cord remains centered on the first belt member.

12. The posterior bracing system of claim 2, wherein each of the plurality of telescopic panels includes a buckle attachment aperture for retention of a buckle of a support strap.

13. An orthopedic brace, comprising:

a posterior panel;

a posterior cover positioned over a portion of a posterior surface of the posterior panel and coupled to the posterior panel, the posterior cover being configured to create a first chamber partially formed between an anterior facing surface of the posterior cover and the posterior facing surface of the posterior panel including a guide channel formed by the posterior facing surface of the posterior panel;

a pulley cover coupled to the posterior cover to create a second chamber partially formed by an anterior facing surface of the pulley cover and a posterior facing surface of the posterior cover and configured to house a pulley subsystem including a plurality of pulley bases, wherein a first pulley base of the plurality of pulley bases includes (i) a first flange extending toward a first edge of the guide channel, the first edge of the guide channel including at least a first stop that, upon the first flange coming into contact with the first stop, prevents further lateral movement of the first pulley base towards a first opening and (ii) a second flange extending towards a second edge of the guide channel, the second edge of the guide channel including at least a second stop positioned in alignment with the first stop so that, upon the first flange coming into contact with the first stop and the second flange coming into contact with the second stop, further lateral movement of the first pulley base towards the first opening is prevented.

14. The orthopedic brace of claim 13, wherein the first chamber is configured to house a plurality of telescopic panels each arranged to partially extend laterally outward of the first chamber, rigid in form, and configured to bend in a concave manner towards a front of the orthopedic brace to provide lateral support for the wearer of the orthopedic brace.

15. The orthopedic brace of claim 14, wherein the guide channel enabling lateral movement of (i) the first pulley base of the plurality of pulley bases between the first opening within the second chamber and a central area of the second chamber and (ii) a second pulley base of the plurality of pulley bases between a second opening within the second chamber and the central area of the second chamber.

16. The orthopedic brace of claim 15, wherein the first opening of the second chamber being positioned on an opposite side of the second chamber as the second opening.

17. The orthopedic brace of claim 15, wherein a first belt member is attached to the first pulley base and a second belt member is attached to the second pulley base.

18. The orthopedic brace of claim 17, wherein the first belt member associated with the first pulley base is attached to a first telescopic panel of the plurality of telescopic panels so that the first belt member moves concurrently with the first telescopic panel.

19. The orthopedic brace of claim 18, wherein the first belt member is extended from the second chamber when the first telescopic panel is extended from the first chamber and the first belt member retreats within the second chamber when the first telescopic panel retreats within from the first chamber.

20. The orthopedic brace of claim 14, wherein each of the plurality of telescopic panels includes a main panel region and a retention panel region, the main panel region of a first telescopic panel corresponding to a first portion of the first telescopic panel removable from the first chamber and the retention panel region corresponds to a second portion of the first telescopic panel configured to be retained within the first chamber.

21. The orthopedic brace of claim 20, wherein the retention panel region of the first telescopic panel includes a first tab portion and a second tab portion that contact posts of the posterior cover operating as stops to prevent complete removal of the first telescopic panel from the first chamber.

22. The orthopedic brace of claim 14, wherein the first pulley base including a first belt slot to which a first belt member is attached and a second pulley base including a second belt slot to which a second belt member is attached, each of the first belt member and the second belt member includes indicia for internal or external sizing of the first belt member and the second belt member.

23. The orthopedic brace of claim 14, wherein a first belt member is attached to the first pulley base and a first telescopic panel of the plurality of telescopic panels, the first telescopic panel including indicia for aligning with an indicia for sizing the first belt member to set a degree of extension and retraction of the first telescopic panel from the first chamber.

24. The orthopedic brace of claim 20, wherein the pulley cover includes a first aperture to receive a first pulley cord to control movement of the first pulley base by causing retraction of a first belt member into the second chamber and retraction of the first telescopic panel of the plurality of telescopic panels into the first chamber, where the first aperture retains that the first pulley cord remains centered on the first belt member.

25. A posterior bracing system deployed as part of an orthopedic brace, comprising:

a posterior panel;

a posterior cover coupled to the posterior panel, wherein the posterior cover includes an anterior facing surface and a posterior facing surface wherein the posterior facing surface of the posterior cover includes a guide channel, the posterior cover being configured to create a first chamber partially formed by the anterior facing surface of the posterior cover and a posterior facing surface of the posterior panel, wherein the first chamber is configured to house a plurality of rigid, telescopic panels each arranged to extend laterally outward of the first chamber; and a pulley cover coupled to the posterior cover to create a second chamber partially formed by an anterior facing surface of the pulley cover and the guide channel of the posterior cover, wherein the second chamber is configured to house a pulley subsystem and provide lateral movement of a plurality of pulley bases including (i) a first pulley base positioned within the guide channel between a first opening within the second chamber and a central area of the second chamber and (ii) a second pulley base positioned within the guide channel between a second opening within the second chamber and the central area of the second chamber, wherein the first pulley base includes (i) a first flange extending toward a first edge of the guide channel and (ii) a second flange extending towards a second edge of the guide channel, wherein the first edge of the guide channel includes at least a first stop that, upon the first flange coming into contact with the first stop, prevents further lateral movement of the first pulley base towards the first opening.

* * * * *